(12) United States Patent
Okazaki et al.

(10) Patent No.: US 9,888,905 B2
(45) Date of Patent: Feb. 13, 2018

(54) MEDICAL DIAGNOSIS APPARATUS, IMAGE PROCESSING APPARATUS, AND METHOD FOR IMAGE PROCESSING

(71) Applicant: Toshiba Medical Systems Corporation, Otawara-shi (JP)

(72) Inventors: Tomoya Okazaki, Kawasaki (JP); Yukinobu Sakata, Kawasaki (JP); Tomoyuki Takeguchi, Kawasaki (JP); Yasuhiko Abe, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 64 days.

(21) Appl. No.: 14/859,492

(22) Filed: Sep. 21, 2015

(65) Prior Publication Data

US 2016/0093044 A1    Mar. 31, 2016

(30) Foreign Application Priority Data

Sep. 29, 2014  (JP) .................................. 2014-199311

(51) Int. Cl.
*G06K 9/00* (2006.01)
*A61B 8/08* (2006.01)
(Continued)

(52) U.S. Cl.
CPC .............. *A61B 8/483* (2013.01); *A61B 8/466* (2013.01); *A61B 8/467* (2013.01); *A61B 8/5207* (2013.01);
(Continued)

(58) Field of Classification Search
CPC ............ G06T 2207/10136; G06T 2207/10132
See application file for complete search history.

(56) References Cited

U.S. PATENT DOCUMENTS 5,782,762 A  *  7/1998  Vining .................. G06T 7/0012
128/920
5,859,891 A  *  1/1999  Hibbard ................ G06T 7/0012
378/62
(Continued)

FOREIGN PATENT DOCUMENTS

| JP | 2009-112436 A | 5/2009 |
| JP | 2015-213745 A | 12/2015 |
| JP | 2016-101482 A | 6/2016 |

*Primary Examiner* — Avinash Yentrapati
(74) *Attorney, Agent, or Firm* — Oblon, McClelland, Maier & Neustadt, L.L.P.

(57) ABSTRACT

A medical diagnosis apparatus of embodiments includes a scanner and processing circuitry. The scanner configured to scan a three-dimensional region including a target region and acquire data of the three-dimensional region. The processing circuitry is configured to discretely arrange fixed points framing three-dimensional shape of the target region in a first medical image based on the data. The processing circuitry is configured to set a boundary of region of interest (ROI) on the three-dimensional shape of the target region according to a position of the fixed point. The processing circuitry is configured to receive an instruction to change a position of the boundary from an input device controlled by a user. The processing circuitry is configured to change the position of the boundary based on a position or positions of at least one of the fixed points according to the instruction while maintaining positions of the fixed points.

20 Claims, 13 Drawing Sheets

(51) Int. Cl.
*A61B 8/00* (2006.01)
*G06T 7/00* (2017.01)
*G06T 7/246* (2017.01)

(52) U.S. Cl.
CPC ............ *G06T 7/0016* (2013.01); *G06T 7/251* (2017.01); *A61B 8/488* (2013.01); *G06T 2207/10136* (2013.01); *G06T 2207/20101* (2013.01); *G06T 2207/30048* (2013.01)

(56) References Cited

U.S. PATENT DOCUMENTS

| | | | | |
|---|---|---|---|---|
| 6,106,466 | A * | 8/2000 | Sheehan | A61B 5/1075 128/916 |
| 6,606,091 | B2 * | 8/2003 | Liang | G06T 17/20 345/424 |
| 7,428,334 | B2 * | 9/2008 | Schoisswohl | G06T 7/0012 382/128 |
| 8,126,244 | B2 * | 2/2012 | Lu | G06F 19/3406 382/128 |
| 8,160,345 | B2 * | 4/2012 | Pavlovskaia | G06T 7/13 382/131 |
| 8,265,363 | B2 * | 9/2012 | Orderud | A61B 8/08 345/420 |
| 8,617,171 | B2 * | 12/2013 | Park | G06T 7/0012 606/87 |
| 9,001,123 | B1 * | 4/2015 | Ames | G06T 17/205 345/419 |
| 2001/0024516 | A1 * | 9/2001 | Yoshioka | A61B 8/08 382/128 |
| 2002/0102023 | A1 * | 8/2002 | Yamauchi | G06F 19/3437 382/199 |
| 2002/0136440 | A1 * | 9/2002 | Yim | G06T 17/20 382/131 |
| 2003/0097219 | A1 * | 5/2003 | O'Donnell | G06T 7/0012 702/19 |
| 2004/0090438 | A1 * | 5/2004 | Alliez | G06T 17/20 345/423 |
| 2004/0249270 | A1 * | 12/2004 | Kondo | G06T 15/08 600/425 |
| 2005/0238216 | A1 * | 10/2005 | Yoden | G06T 7/215 382/128 |
| 2006/0064007 | A1 * | 3/2006 | Comaniciu | G06T 7/277 600/416 |
| 2006/0072802 | A1 * | 4/2006 | Higgs | G06T 7/149 382/131 |
| 2006/0094951 | A1 * | 5/2006 | Dean | A61F 2/30942 600/407 |
| 2006/0110037 | A1 * | 5/2006 | Kaus | G06T 7/149 382/173 |
| 2006/0126922 | A1 * | 6/2006 | Von Berg | G06T 7/0012 382/154 |
| 2006/0149511 | A1 * | 7/2006 | Kaus | G06T 7/149 703/2 |
| 2006/0241445 | A1 * | 10/2006 | Altmann | A61B 8/12 600/443 |
| 2006/0253024 | A1 * | 11/2006 | Altmann | A61B 8/12 600/437 |
| 2006/0253031 | A1 * | 11/2006 | Altmann | G06T 7/38 600/466 |
| 2006/0285758 | A1 * | 12/2006 | Marugame | G06T 9/001 382/236 |
| 2007/0297674 | A1 * | 12/2007 | Declerck | G06T 3/00 382/173 |
| 2008/0069436 | A1 * | 3/2008 | Orderud | G06T 7/20 382/154 |
| 2008/0123927 | A1 * | 5/2008 | Miga | A61B 90/36 382/131 |
| 2008/0137926 | A1 * | 6/2008 | Skinner | G06K 9/34 382/131 |
| 2008/0304730 | A1 * | 12/2008 | Abe | A61B 8/08 382/131 |
| 2009/0238404 | A1 * | 9/2009 | Orderud | G06F 19/3437 382/103 |
| 2009/0297012 | A1 * | 12/2009 | Brett | G06K 9/6209 382/132 |
| 2009/0310835 | A1 * | 12/2009 | Kaus | G06T 17/20 382/128 |
| 2010/0195881 | A1 * | 8/2010 | Orderud | A61B 8/08 382/131 |
| 2010/0195887 | A1 * | 8/2010 | Abe | A61B 8/08 382/131 |
| 2012/0281895 | A1 * | 11/2012 | Chono | A61B 8/461 382/128 |
| 2013/0135305 | A1 * | 5/2013 | Bystrov | G06T 19/20 345/420 |
| 2013/0182935 | A1 * | 7/2013 | Wang | G06K 9/3233 382/133 |
| 2014/0126797 | A1 * | 5/2014 | Kaus | G06T 17/20 382/131 |
| 2014/0334706 | A1 * | 11/2014 | Toma | A61B 8/0883 382/131 |
| 2015/0045605 | A1 * | 2/2015 | Hirai | A61N 5/103 600/1 |
| 2015/0173707 | A1 * | 6/2015 | Ohuchi | A61B 8/0883 345/424 |
| 2015/0305707 | A1 | 10/2015 | Okazaki et al. | |
| 2015/0342571 | A1 * | 12/2015 | Ohuchi | A61B 8/0883 382/128 |
| 2016/0140707 | A1 * | 5/2016 | Abe | G06T 15/00 382/131 |
| 2016/0192993 | A1 * | 7/2016 | Bodduluri | A61F 2/10 382/128 |

* cited by examiner

FIG.6
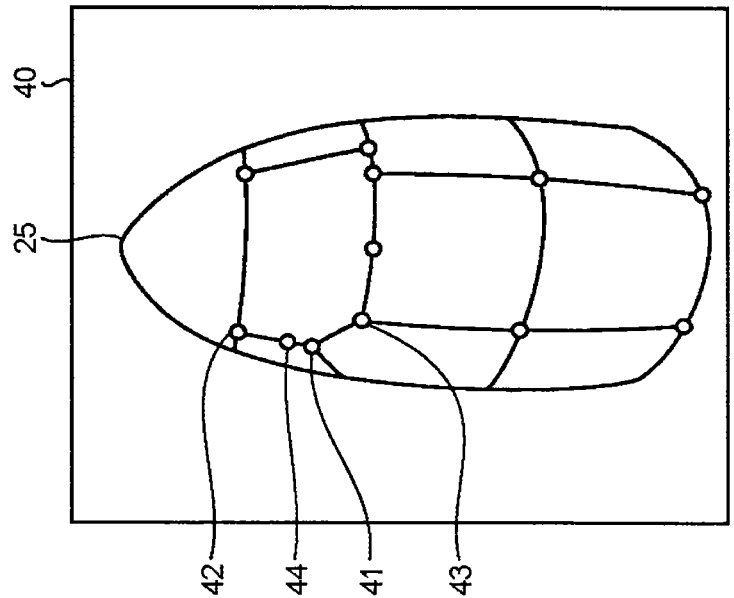
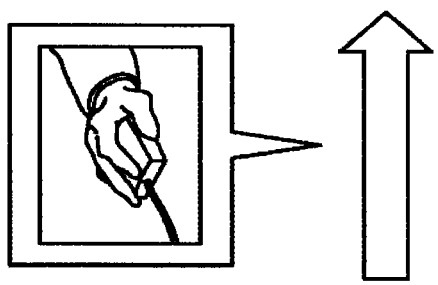
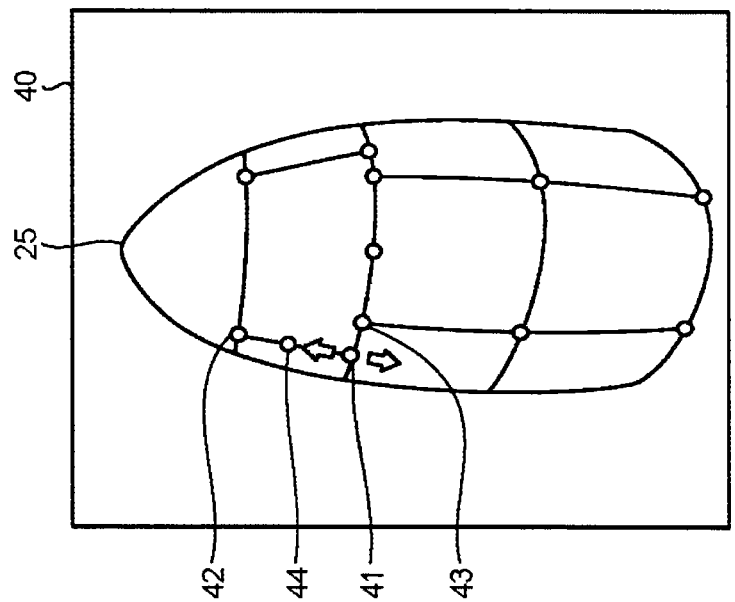

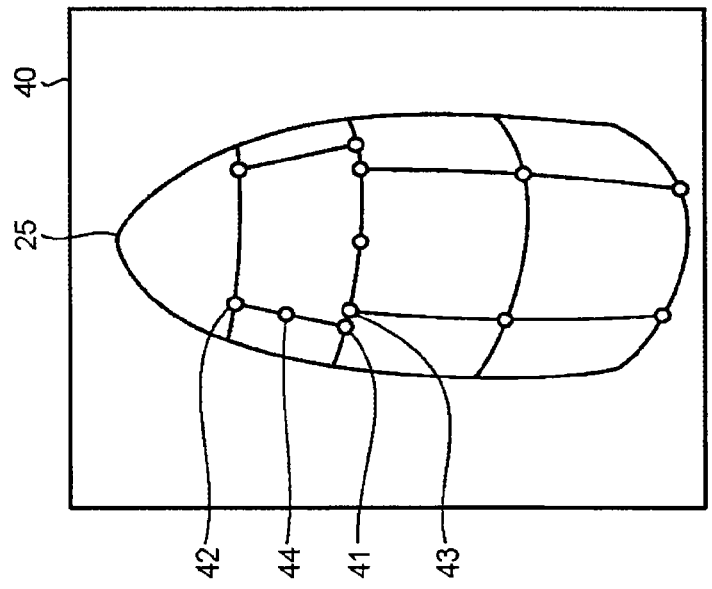
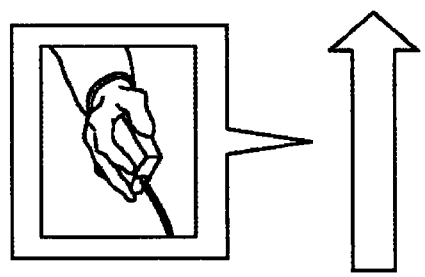
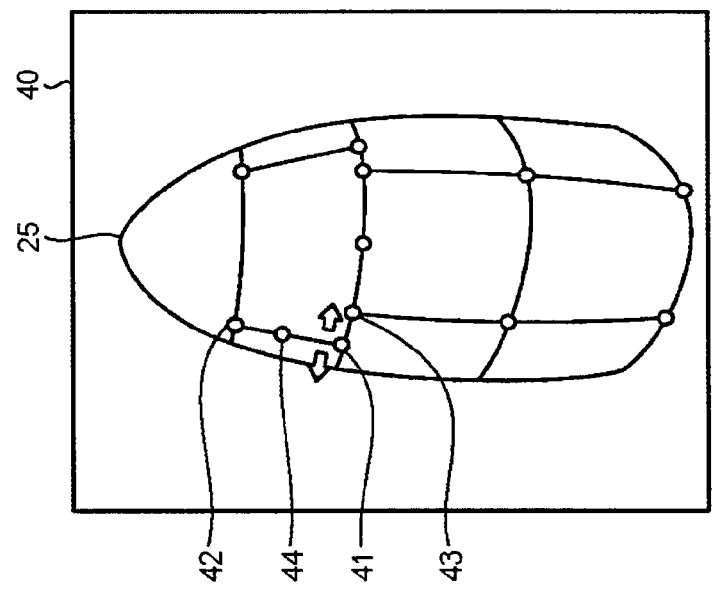
FIG.7

| REGION OF HEART | SEGMENT PATTERN |
|---|---|
| LEFT VENTRICLE | 17-SEGMENT |
| RIGHT VENTRICLE | 7-SEGMENT |
| ⋮ | ⋮ |

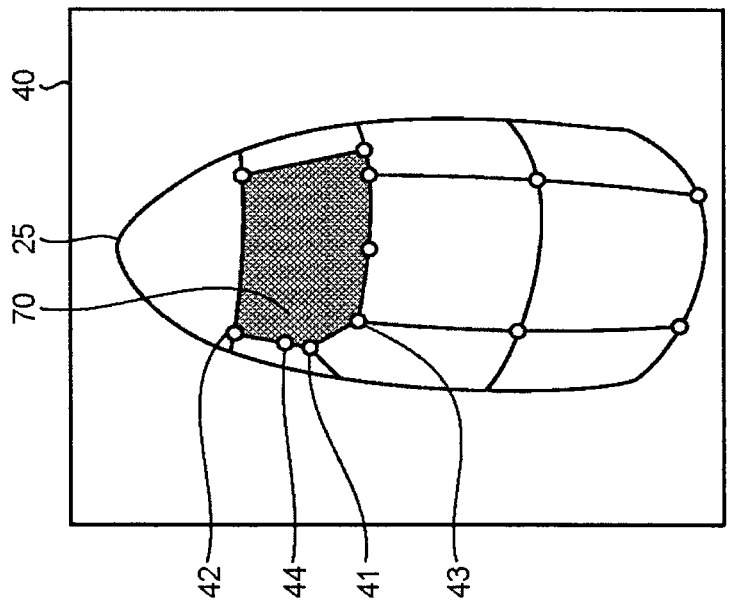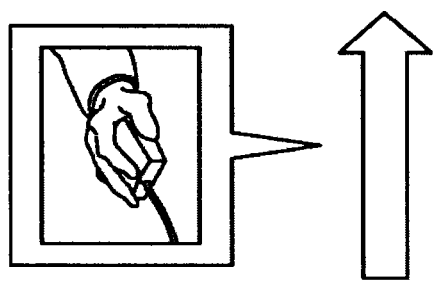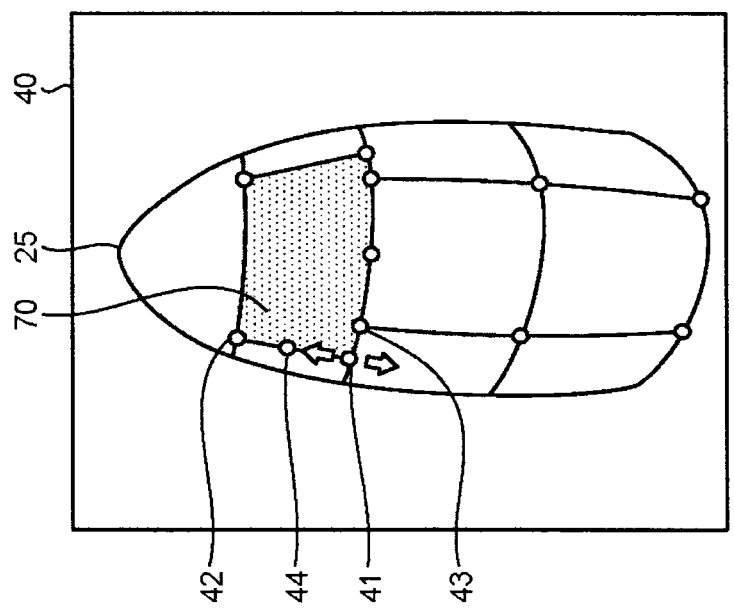
FIG.13

MEDICAL DIAGNOSIS APPARATUS, IMAGE PROCESSING APPARATUS, AND METHOD FOR IMAGE PROCESSING

CROSS-REFERENCE TO RELATED APPLICATIONS

This application is based upon and claims the benefit of priority from Japanese Patent Application No. 2014-199311, filed on Sep. 29, 2014; the entire contents of which are incorporated herein by reference.

FIELD

Embodiments described herein relate generally to a medical diagnosis apparatus, an image processing apparatus, and a method for image processing.

BACKGROUND

Techniques are conventionally available for objectively and quantitatively evaluating a cardiac function by obtaining motion information, such as displacements and distortion of a tissue, of the heart. For example, a technique for ultrasound diagnostic imaging is available in which the motion of the heart is estimated by chronologically collecting ultrasound images of the heart, performing pattern matching of local regions on the ultrasound images, and tracking the local regions.

In the case of dealing with a two-dimensional medical image, a boundary of region of interest (ROI) is easily adjusted by user control on the image displayed on a monitor. For example, the direction and distance of movement of the boundary of region in the plane of a screen are associated in advance with an operation (such as a drag-and-drop operation) of an input device so that the boundary of the region of interest is adjusted by only control of the input device in the case in which an ultrasound image of a heart muscle is displayed in a divided manner in a plurality of regions in a cross-section of the heart.

BRIEF DESCRIPTION OF THE DRAWINGS

FIG. 6 is a diagram for explaining processing performed by an adjuster according to the first embodiment;

FIG. 7 is a diagram for explaining the processing performed by the adjuster according to the first embodiment;

FIG. 13 is a diagram for explaining processing performed by the display controller according to the second embodiment;

DETAILED DESCRIPTION

A medical diagnosis apparatus of embodiments includes a scanner and processing circuitry. The scanner configured to scan a three-dimensional region including a target region and acquire data of the three-dimensional region. The processing circuitry is configured to discretely arrange fixed points framing three-dimensional shape of the target region in a first medical image based on the data. The processing circuitry is configured to set a boundary of region of interest (ROI) on the three-dimensional shape of the target region according to a position of the fixed point. The processing circuitry is configured to receive an instruction to change a position of the boundary from an input device controlled by a user. The processing circuitry is configured to change the position of the boundary based on a position or positions of at least one of the fixed points according to the instruction while maintaining positions of the fixed points.

The following describes a medical diagnosis apparatus, an image processing apparatus, and a method for image processing according to each of the embodiments, with reference to the drawings.

The following describes a case in which each of the embodiments is applied to an ultrasonic diagnostic apparatus as an example of the medical diagnosis apparatus. Embodiments are, however, not limited to this example. For example, the case may be such that each of the embodiments is applied to, for example, an X-ray diagnostic apparatus, an X-ray computed tomography (CT) apparatus, a magnetic resonance imaging (MRI) apparatus, a single-photon emission computed tomography (SPECT) apparatus, a positron emission tomography (PET) apparatus, a SPECT-CT apparatus obtained by integrating the SPECT apparatus with the X-ray CT apparatus, a PET-CT apparatus obtained by integrating the PET apparatus with the X-ray CT apparatus, a PET-MRI apparatus obtained by integrating the PET apparatus with the MRI apparatus, or an apparatus group including these apparatuses.

First Embodiment

Figure 1:
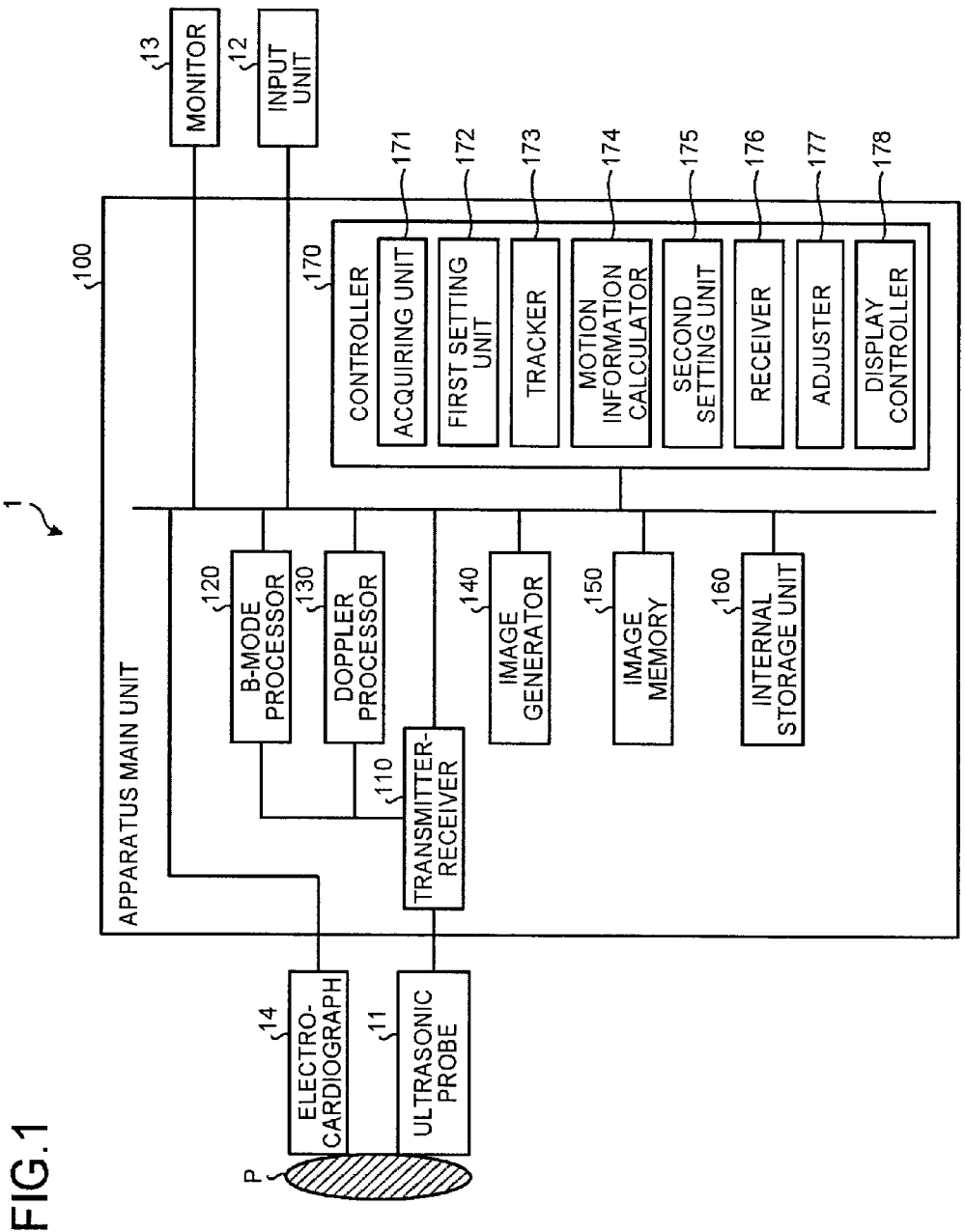
FIG. 1 is a block diagram illustrating a configuration example of an ultrasonic diagnostic apparatus according to a first embodiment.

FIG. 1 is a block diagram illustrating a configuration example of an ultrasonic diagnostic apparatus according to a first embodiment. As illustrated in FIG. 1, this ultrasonic diagnostic apparatus 1 according to the first embodiment includes an ultrasonic probe 11, an input unit 12, a monitor 13, an electrocardiograph 14, and an apparatus main unit 100.

The ultrasonic probe 11 includes a plurality of piezoelectric transducer elements, which generate ultrasonic waves based on drive signals supplied from a transmitter-receiver 110 included in the apparatus main unit 100 (to be described later). The ultrasonic probe 11 receives reflected waves from a subject P, and converts them into electric signals. The ultrasonic probe 11 also includes a matching layer provided on the transducer elements and a backing material for preventing the ultrasonic waves from being propagated backward from the transducer elements. The ultrasonic probe 11 is detachably connected to the apparatus main unit 100.

When the ultrasonic probe 11 transmits the ultrasonic waves to the subject P, the transmitted ultrasonic waves are successively reflected by discontinuous surfaces of acoustic impedance in the body tissue of the subject P, and are received as reflected wave signals by the piezoelectric transducer elements included in the ultrasonic probe 11. The amplitudes of the reflected wave signals received depend on differences in acoustic impedance of the discontinuous surfaces reflecting the ultrasonic waves. When the transmitted ultrasonic pulses are reflected by a surface of, for example, a moving bloodstream or a heart wall, the reflected wave signals are shifted in frequency by a Doppler effect depending on the velocity component of the moving body with respect to the direction of transmission of the ultrasonic waves.

For example, in the present embodiment, a mechanical 4D probe or a 2D array probe is connected to the apparatus main unit 100, as the ultrasonic probe 11 for three-dimensional scanning of the subject P. The mechanical 4D probe can perform two-dimensional scanning by using the piezoelectric transducer elements arranged in a row like a 1D array probe, or can perform the three-dimensional scanning by oscillating the piezoelectric transducer elements at a certain angle (oscillation angle). The 2D array probe can perform the three-dimensional scanning by using the piezoelectric transducer elements arranged in a matrix, or can perform the two-dimensional scanning by focusing and transmitting the ultrasonic waves.

The input unit 12 includes, for example, a mouse, a keyboard, buttons, panel switches, a touch command screen, a foot switch, a track ball, and a joystick. The input unit 12 receives various setting requests from the user of the ultrasonic diagnostic apparatus, and forwards the received various setting requests to the apparatus main unit 100.

The monitor 13 displays a graphical user interface (GUI) used by the user of the ultrasonic diagnostic apparatus to enter the various setting requests with the input unit 12, and displays, for example, ultrasound image data generated by the apparatus main unit 100.

The electrocardiograph 14 acquires an electrocardiogram (ECG) waveform of the subject P as a biosignal of the subject P subjected to the ultrasound scan. The electrocardiograph 14 transmits the acquired ECG waveform to the apparatus main unit 100.

The apparatus main unit 100 is an apparatus that generates the ultrasound image data based on the reflected wave signals received by the ultrasonic probe 11. The apparatus main unit 100 illustrated in FIG. 1 is an apparatus that can generate two-dimensional ultrasound image data based on two-dimensional reflected wave data received by the ultrasonic probe 11. The apparatus main unit 100 illustrated in FIG. 1 is also an apparatus that can generate three-dimensional ultrasound image data based on three-dimensional reflected wave data received by the ultrasonic probe 11. The three-dimensional ultrasound image data is an example of "three-dimensional medical image data" or "volume data".

As illustrated in FIG. 1, the apparatus main unit 100 includes the transmitter-receiver 110, a B-mode processor 120, a Doppler processor 130, an image generator 140, an image memory 150, an internal storage unit 160, and a controller 170.

The transmitter-receiver 110 includes, for example, a pulse generator, a transmission delay unit, and a pulser, and supplies the drive signals to the ultrasonic probe 11. The pulse generator repetitively generates rate pulses for forming the ultrasonic waves to be transmitted at a predetermined rate frequency. The transmission delay unit focuses the ultrasonic waves generated by the ultrasonic probe 11 into a beam, and gives each of the rate pulses generated by the pulse generator a delay time for each of the piezoelectric transducer elements that is necessary to determine transmission directivity. The pulser applies the drive signals (drive pulses) to the ultrasonic probe 11 at times based on the rate pulses. That is, the transmission delay unit changes the delay time given to each of the rate pulses so as to freely adjust the direction of transmission of the ultrasonic waves transmitted from surfaces of the piezoelectric transducer elements.

The transmitter-receiver 110 has a function capable of instantaneously changing, for example, a transmission frequency and a transmission drive voltage in order to execute a predetermined scan sequence according to an instruction of the controller 170 (to be described later). In particular, the transmission drive voltage can be changed by a linear amplifier type transmission circuit capable of instantaneously switching the value thereof or by a mechanism for electrically switching power supply units.

The transmitter-receiver 110 also includes, for example, a preamplifier, an analog/digital (A/D) converter, a reception delay unit, and an adder, and applies various types of processing to the reflected wave signals received by the ultrasonic probe 11 to generate the reflected wave data. The preamplifier amplifies the reflected wave signals for each channel. The A/D converter converts the amplified reflected wave signals into digital signals. The reception delay unit gives the digital signals a delay time necessary to determine reception directivity. The adder applies addition processing to the reflected wave signals processed by the reception delay unit to generate the reflected wave data. The addition processing by the adder enhances reflection components from a direction corresponding to the reception directivity of the reflected wave signals, and the reception directivity and the transmission directivity form a comprehensive beam of ultrasonic transmission and reception.

When a two-dimensional region of the subject P is scanned, the transmitter-receiver 110 causes ultrasonic beams to be transmitted in two-dimensional directions from the ultrasonic probe 11. The transmitter-receiver 110 then generates the two-dimensional reflected wave data from the reflected wave signals received by the ultrasonic probe 11. When a three-dimensional region of the subject P is scanned, the transmitter-receiver 110 causes the ultrasonic beams to be transmitted in three-dimensional directions from the ultrasonic probe 11. The transmitter-receiver 110 then generates the three-dimensional reflected wave data from the reflected wave signals received by the ultrasonic probe 11.

The form of output signals from the transmitter-receiver 110 can be variously selected, including, for example, signals called radio frequency (RF) signals that include phase information, or signals that include amplitude information after envelope detection processing.

The B-mode processor 120 receives the reflected wave data from the transmitter-receiver 110, and performs, for example, logarithmic amplification and the envelope detection processing to generate data (B-mode data) in which signal intensity is expressed by a degree of luminance.

The Doppler processor 130 applies frequency analysis to velocity information obtained from the reflected wave data received from the transmitter-receiver 110, and extracts components of the bloodstream, the tissue, and a contrast agent echo based on the Doppler effect. Then, the Doppler processor 130 generates data (Doppler data) obtained by extracting moving body information, such as a velocity, variance, and power, for multiple points.

The B-mode processor 120 and the Doppler processor 130 according to the first embodiment can process both the two-dimensional and three-dimensional reflected wave data. Specifically, the B-mode processor 120 generates two-dimensional B-mode data from the two-dimensional reflected wave data, and generates three-dimensional B-mode data from the three-dimensional reflected wave data. The Doppler processor 130 generates two-dimensional Doppler data from the two-dimensional reflected wave data, and generates three-dimensional Doppler data from the three-dimensional reflected wave data.

The image generator 140 generates the ultrasound image data from the data generated by the B-mode processor 120 and the Doppler processor 130. Specifically, the image generator 140 generates two-dimensional B-mode image data expressing the intensity of reflected waves by luminance, from the two-dimensional B-mode data generated by the B-mode processor 120. The image generator 140 also generates two-dimensional Doppler image data representing the moving body information, from the two-dimensional Doppler data generated by the Doppler processor 130. The two-dimensional Doppler image data is velocity image data, variance image data, power image data, or a combination of such data. The image generator 140 can also generate a Doppler waveform obtained by plotting the velocity information of the bloodstream and the tissue along time, from the Doppler data generated by the Doppler processor 130.

In general, the image generator 140 converts (using scan conversion) a scan line signal string of ultrasound scan into a scan line signal string in a video format typified by, for example, a television format, and thus generates ultrasound image data for display. Specifically, the image generator 140 generates the ultrasound image data for display by performing coordinate transformation according to the form of ultrasound scanning by the ultrasonic probe 11. The image generator 140 performs, in addition to the scan conversion, various types of image processing, such as image processing (smoothing processing) to regenerate an average luminance image using a plurality of image frames after the scan conversion or image processing (edge enhancement processing) using a differential filter in the image. The image generator 140 also combines the ultrasound image data with, for example, text information on various parameters, scale marks, and a body mark.

That is, the B-mode data and the Doppler data are ultrasound image data before the scan conversion processing, and the data generated by the image generator 140 is ultrasound image data for display after the scan conversion processing. The B-mode data and the Doppler data are also called raw data.

Moreover, the image generator 140 applies the coordinate transformation to the three-dimensional B-mode data generated by the B-mode processor 120 so as to generate three-dimensional B-mode image data. The image generator 140 also applies the coordinate transformation to the three-dimensional Doppler data generated by the Doppler processor 130 so as to generate three-dimensional Doppler image data. That is, the image generator 140 generates the "three-dimensional B-mode image data and three-dimensional Doppler image data" as the "three-dimensional ultrasound image data (volume data)".

Furthermore, the image generator 140 applies rendering processing to the volume data so as to generate various types of two-dimensional image data for displaying the volume data on the monitor 13. Examples of the rendering processing performed by the image generator 140 include processing using a multi-planer reconstruction (MPR) method to generate MPR image data from the volume data. Examples of the rendering processing performed by the image generator 140 also include processing of applying curved MPR to the volume data and processing of performing a maximum intensity projection to the volume data. Examples of the rendering processing performed by the image generator 140 further include volume rendering (VR) processing.

The image memory 150 is a memory that stores the image data for display generated by the image generator 140. The image memory 150 can also store the data generated by the B-mode processor 120 and the data generated by the Doppler processor 130. The B-mode data and the Doppler data stored in the image memory 150 can be called up, for example, by the user after a diagnosis, and are converted into the ultrasound image data for display via the image generator 140.

The image generator 140 stores the ultrasound image data and time of the ultrasound scan performed to generate the ultrasound image data in the image memory 150 in a manner associated with the ECG waveform received from the electrocardiograph 14. The controller 170 (to be described later) can obtain a cardiac time phase during the ultrasound scan performed to generate the ultrasound image data, by referring to the data stored in the image memory 150.

The internal storage unit 160 stores control programs for performing the ultrasonic transmission and reception, the image processing, and display processing, and also stores diagnostic information (such as a patient ID and findings of a doctor) and various types of data, such as diagnostic protocols and various body marks. The internal storage unit 160 is also used for saving the image data stored in the image memory 150 as needed. The data stored in the internal storage unit 160 can be transmitted to an external device via an interface (not illustrated). Examples of the external device include, but are not limited to, high-performance workstations for image processing, personal computers (PCs) used by doctors performing image diagnosis, storage media such as CDs and DVDs, and printers.

The controller 170 controls overall processing of the ultrasonic diagnostic apparatus. Specifically, the controller 170 controls processing performed by the transmitter-receiver 110, the B-mode processor 120, the Doppler processor 130, and the image generator 140, based on the various setting requests entered by the user via the input unit 12 and on the various control programs and the various types of data read from the internal storage unit 160. The controller 170 also controls the monitor 13 to display the ultrasound image data for display stored in the image memory 150 or the internal storage unit 160.

The controller 170 provides motion information of a periodically moving tissue. For example, the controller 170 acquires ultrasound image data of the heart stored in the image memory 150, and performs cardiac wall motion tracking (WMT) using image processing to calculate motion information of the heart wall. The controller 170 stores the motion information thus generated in the image memory 150 and/or the internal storage unit 160. The processing of calculating the motion information by the controller 170 will be described later.

In the case of dealing with a two-dimensional medical image, a boundary of region of interest is easily adjusted by user control on an image displayed on a monitor. For example, the direction and distance of movement of the boundary of region in the plane of a screen are associated in advance with an operation (such as a drag-and-drop operation) of an input device so that the boundary of the region of interest is adjusted by only control of the input device in the case in which an ultrasound image of a heart muscle is displayed in a divided manner in a plurality of regions in a cross-section of the heart.

In the case of dealing with a three-dimensional medical image, however, the boundary of the region of interest is difficult to be adjusted (changed) by the user control on the image displayed on the monitor, unlike in the case of the two-dimensional medical image. For example, when a region of interest is enlarged (or reduced) in a certain cross-section, the enlargement (or reduction) applies only to the cross-section. As a result, to three-dimensionally adjust the boundary of the region of interest, each of the ROIs set in a plurality of cross-sections needs to be adjusted, resulting in a complicated operation. This makes it difficult to adjust the boundary of the region of interest in the three-dimensional image.

For example, when a region of interest is adjusted in an image displayed using the volume rendering processing, only two-dimensional information on the plane of the screen can be specified by, for example, the drag-and-drop operation, and no depth information can be specified. This also makes it difficult to adjust the boundary of the region of interest in the three-dimensional image.

Hence, in order to allow easy adjustment of the boundary of the region of interest in the three-dimensional image, the ultrasonic diagnostic apparatus 1 according to the first embodiment includes the following configuration.

The controller 170 according to the first embodiment includes an acquiring unit 171, a first setting unit 172, a tracker 173, a motion information calculator 174, a second setting unit 175, a receiver 176, an adjuster 177, and a display controller 178. The controller 170 is an example of the processing circuitry.

The following describes a case in which the controller 170 performs the cardiac wall motion tracking to calculate the motion information of the heart wall. Embodiments are, however, not limited to this example. The controller 170 is not limited to perform the wall motion tracking, but can also, for example, calculate thickness information of the heart muscle.

The acquiring unit 171 acquires three-dimensional medical image data obtained by photographing the heart. For example, the acquiring unit 171 acquires a volume data group including a plurality of pieces of volume data for at least one heartbeat.

For example, the user uses a sector probe to two-dimensionally or three-dimensionally scan a region including the heart of the subject P, and captures dynamic image data of two-dimensional or three-dimensional ultrasound image data in which the heart muscle is depicted. This dynamic image data is, for example, an ultrasound image data group collected in the B mode. This user control causes the image generator 140 to generate the dynamic image data of the heart muscle and store the generated dynamic image data in the image memory 150. The user then sets an interval for one heartbeat, for example, from an R wave to the next R wave in an electrocardiogram, as a target interval of processing.

The present embodiment can be applied to a case in which the target interval of processing is set to be an interval for two heartbeats or an interval for three heartbeats.

Then, for example, the acquiring unit 171 acquires the volume data group from the image memory 150. The volume data group includes a plurality of frames of ultrasound volume data (three-dimensional ultrasound image data) included in the interval for one heartbeat set by the user.

In the first embodiment, a case will be described in which the acquiring unit 171 acquires the three-dimensional ultrasound image data as the three-dimensional medical image data, and uses the three-dimensional ultrasound image data in the following processing. Embodiments are, however, not limited to this example. For example, the acquiring unit 171 only needs to acquire the three-dimensional medical image data obtained by photographing the heart. The acquiring unit 171 need not acquire the three-dimensional medical image data obtained by photographing the entire heart. That is, the acquiring unit 171 only needs to acquire the three-dimensional medical image data obtained by photographing at least a part of the heart, such as the left ventricle or the right ventricle of the heart.

The first setting unit 172 sets identification information for identifying each position among a plurality of positions representing a three-dimensional shape of at least a part of the heart in the three-dimensional medical image data. For example, the first setting unit 172 sets a plurality of fixed points with addresses assigned thereto in positions corresponding to a contour (surface) of a tissue (such as the heart) in at least one piece of the ultrasound image data included in the ultrasound image data group. The addresses are numbers assigned to identify the respective fixed points, and are defined according to the positions of the respective fixed points, for example, in an endocardium of the heart. The addresses are not limited to numbers, but only need to be identification information, such as characters or symbols, enabling identification of the positions of the fixed points. In other words, the first setting unit 172 discretely arranges the fixed points framing the three-dimensional shape of the target region in the first medical image including the target region. The target region is, for example, a heart chamber of the heart.

In the first embodiment, a case will be described in which the following processing is applied to an endocardium of the left ventricle as an example of the surface of the heart. Embodiments are, however, not limited to this example. The following processing is not limited to be applied to an endocardium, but may, for example, be applied to an epicardium, or to an intermediate layer between an endocardium and an epicardium. The following processing is not limited to be applied to the left ventricle, but may be applied to any region, such as the right ventricle, the left atrium, the right atrium, or the entire heart. In the present embodiment, the first setting unit 172 sets the fixed points constituting the contour in positions corresponding to an initial contour of the heart according to information manually set by the user.

First, the user specifies any cardiac time phase for the volume data group acquired by the acquiring unit 171. The cardiac time phase specified here is any one of the frames included in the interval for one heartbeat, and is, for example, an end-diastolic phase (first R-wave phase). After the user sets the cardiac time phase, the first setting unit 172 instructs the image generator 140 to perform the MPR processing of the volume data of the heart in the specified cardiac time phase, and instructs the monitor 13 to display an MPR cross-section (reference MPR cross-section) that serves as a reference during the setting of the initial contour. The above has described the case in which the end-diastolic phase is specified as any cardiac time phase. The cardiac time phase is, however, not limited to this, but may be, for example, an end-systolic phase.

For example, the user specifies to display an apical four-chamber view (A4C) as a first reference MPR cross-section (MPR1) and an apical two-chamber view (A2C) as a second reference MPR cross-section (MPR2). The user then enters the initial contour for each of the apical four-chamber view and the apical two-chamber view. For example, a papillary muscle and a tendinous chord are displayed in the MPR cross-section, in addition to the endocardium and the epicardium of the heart. Hence, the user specifies the initial contours so as not to include, for example, the papillary muscle and the tendinous chord depicted in the MPR cross-section while observing the displayed reference MPR cross-sections in the end-diastolic phase.

After the initial contours are entered for the reference MPR cross-sections, the first setting unit 172 generates a three-dimensional initial contour from the entered two-dimensional initial contours, using a known method. Specifically, the first setting unit 172 generates a three-dimensional initial contour P_endo from the initial contours of the endocardium of the heart specified in MPR1 and MPR2.

The first setting unit 172 then assigns the addresses to the respective fixed points constituting the initial contour of the endocardium of the heart in the three dimensions. The first setting unit 172 defines, for example, the position of each of the fixed points of the endocardium of the heart as P_endo (t,h,d). Here, t represents the frame (cardiac time phase) included in the interval for one heartbeat; h represents an address number in the long axis direction; and d represents an address number in the circumferential direction. In this case, the first R-wave phase is used to set the initial cross-sections, so that t=0.

Figure 2:
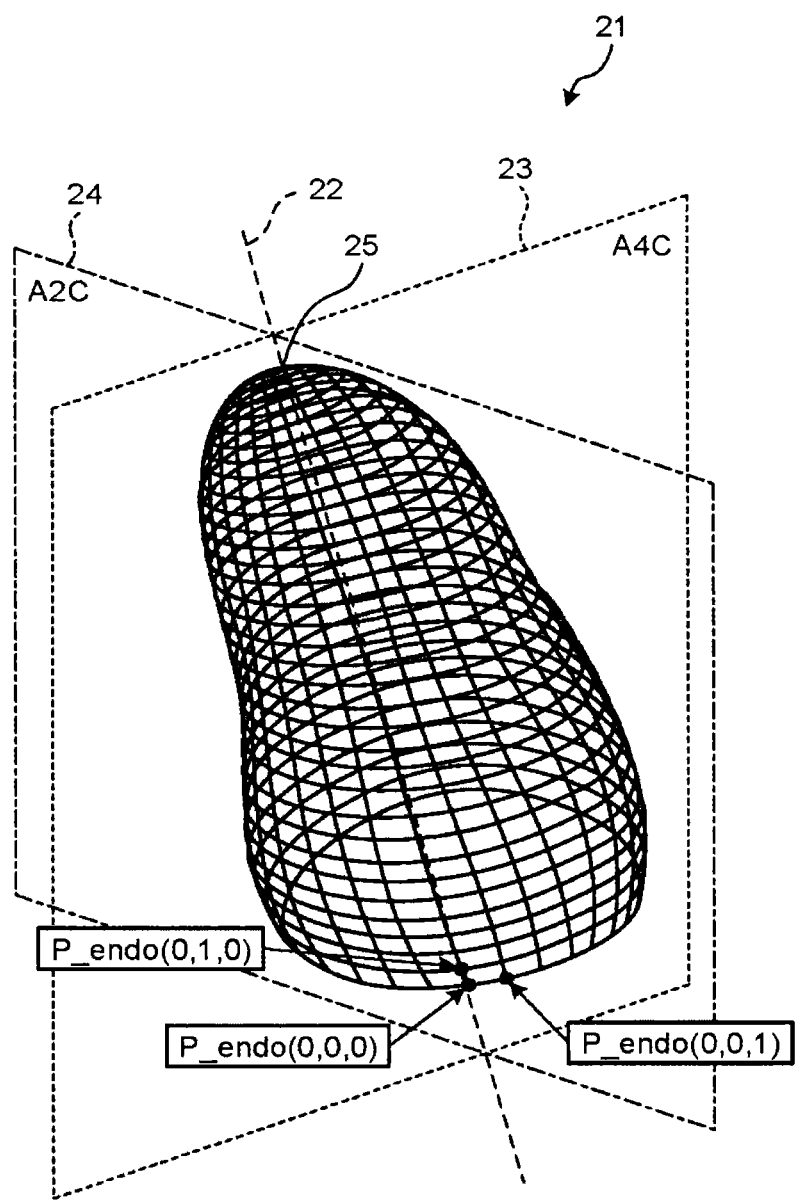
FIG. 2 is a diagram for explaining fixed points set by a first setting unit according to the first embodiment.

FIG. 2 is a diagram for explaining the fixed points set by the first setting unit 172 according to the first embodiment. The example illustrated in FIG. 2 exemplifies a case in which an initial contour 21 is set for the contour of the endocardium of the left ventricle. The fixed points illustrated in FIG. 2 are arranged at intersecting points of the contour of the endocardium of the heart, cross-sections passing through a long axis 22, and cross-sections (short axis cross-sections) orthogonal to the direction of the long axis 22. A plane 23 corresponds to MPR1 (A4C), and a plane 24 corresponds to MPR2 (A2C).

As illustrated in FIG. 2, the first setting unit 172 assumes one of the positions in which the initial contour intersects with MPR1 as a reference position in the circumferential direction, and sets d of a fixed point in that position to 0. Specifically, the position of the fixed point located in this reference position is represented as P_endo(0,h,0). The first setting unit 172 then sequentially sets the address numbers of the fixed points arranged in the circumferential direction starting from the fixed point in the reference position such that d=1, 2, 3, . . . . The first setting unit 172 assumes the position of an annular contour farthest from a cardiac apex 25 on the three-dimensional initial contour 21 as a reference position in the long axis direction, and sets h of a fixed point in that position to 0. Specifically, the position of the fixed point located in this reference position is represented as P_endo(0,0,d). The first setting unit 172 then sequentially sets the address numbers of the fixed points arranged in the direction toward the cardiac apex starting from the fixed point in the reference position such that h=1, 2, 3, . . . .

The case has been described with reference to FIG. 2 in which the fixed points are arranged in the long axis direction and the circumferential direction on the surface of the endocardium of the heart in the three-dimensional ultrasound image data, and thereby, small regions surrounded by the fixed points are formed into quadrilateral patches. Embodiments are, however, not limited to this example. For example, the fixed points may be arranged according to a predetermined rule so that the small regions are formed into triangular patches or other patches, such as polygonal patches or patches including curves.

The case has also been described with reference to FIG. 2 in which the two reference MPR cross-sections are used to specify the initial contour. Embodiments are, however, not limited to this example. For example, the first setting unit 172 may use two or more reference MPR cross-sections to specify the initial contour. The above has described the case in which the apical four-chamber view and the apical two-chamber view are used as the reference MPR cross-sections. The reference MPR cross-sections are, however, not limited to these views. For example, an apical three-chamber view (A3C) may be used as another long axis cross-section passing through the center axis of the left heart chamber; otherwise, a short axis cross-section (such as SAX-A at the cardiac apex level, SAX-M at a middle level, or SAX-B at the base level) orthogonal to the long axis cross-section, or further, a cross-section defined by a positional relation with these cross-sections may be used. The processing of displaying the reference MPR cross-sections is not limited to processing by the manual control as described above. For example, the reference MPR cross-sections may be automatically displayed using automatic cross-section detection, with which any cross-section is automatically detected from the volume data and displayed. The initial contour is not limited to be specified by the manual control described above. The first setting unit 172 may automatically or semi-automatically specify the initial contour using dictionary data of shapes of the contour of the endocardium (such as statistical data of contours set in the past). Moreover, the initial contour may be automatically or semi-automatically specified using, for example, a boundary detection method for detecting a boundary in an image.

The tracker 173 uses the ultrasound image data in which the fixed points are set and other ultrasound image data to perform processing including pattern matching so as to track the positions of the fixed points in the pieces of ultrasound image data included in the ultrasound image data group.

For example, after the fixed points are set in positions corresponding to the initial contour for volume data of a frame t=0 included in the volume data group, the tracker 173 performs processing including pattern matching to track the positions of the fixed points in another frame t. Specifically, the tracker 173 repeatedly performs pattern matching between the volume data of the frame in which the fixed points are already set and volume data of a frame adjacent to the frame with the already set fixed points. That is, the tracker 173 tracks the positions of the fixed points P_endo (t,h,d) in the volume data of each of the frames t=1, 2, 3, . . . , beginning at the fixed points P_endo(0,h,d) of the endocardium of the heart in the volume data of the frame t=0. As a result, the tracker 173 obtains coordinate information of the fixed points constituting the endocardium of the heart for each of the frames included in the interval for one heartbeat. In other words, based on the positions of the fixed points, the tracker 173 performs tracking processing between the first medical image and a second medical image collected in a time phase different from that of the first medical image.

The motion information calculator 174 uses the positions of the fixed points in the pieces of ultrasound image data included in each ultrasound image data group to calculate the motion information representing the motion of the tissue for each of the pieces of ultrasound image data.

Examples of the motion information calculated by the motion information calculator 174 include parameters, such as displacements of the fixed points for one frame and velocities defined as time derivatives of the displacements. The motion information is, however, not limited to these parameters, but only needs to be parameters that can be calculated using the coordinate information of the fixed points in each of the frames included in the interval for one heartbeat. Specifically, the examples of the motion information include various parameters, such as strains each representing a ratio of change in distance between two points in a certain direction, strain rates defined as time derivatives of the strains, and local areas, and rates of change therein from t=0, of the endocardium surface of the heart. Moreover, the user can set any parameters, such as "time until a certain item of the motion information reaches a peak value".

The following describes, as an example, a case in which the motion information calculator 174 calculates a "time derivative value of a local area change rate of the endocardium surface" as the motion information. The calculated motion information is assigned to each of the fixed points used for the calculation. Specifically, for example, the motion information calculated from the fixed points of the endocardium of the heart is defined as V_endo(t,h,d). The motion information calculator 174 stores the calculated motion information in the image memory 150 on a volume data group-by-volume data group basis.

In this way, the motion information calculator 174 calculates the motion information of the endocardium of the heart for the ultrasound image data group. In other words, the motion information calculator 174 calculates the motion information for a region of interest based on the result of the tracking processing.

The second setting unit 175 set a region of interest, a boundary of which passes through any one of the above-described positions. For example, the second setting unit 175 sets a region group including regions adjacent to one another, as a region of interest. The region group refers to, for example, the 16-segment model recommended by the American Society of Echocardiography or the 17-segment model recommended by the American Heart Association, in the case of the left ventricle. No standard segment model is available for heart chambers (such as the right ventricle) other than the left ventricle, so that any segment model is used according to the purpose of use. At least a part of the heart may include one or more regions of interest. If at least a part of the heart includes more than one region of interest, the regions of interest may be adjacent to one another. The regions of interest may be in contact with one another at a point or along a line.

Figure 3:
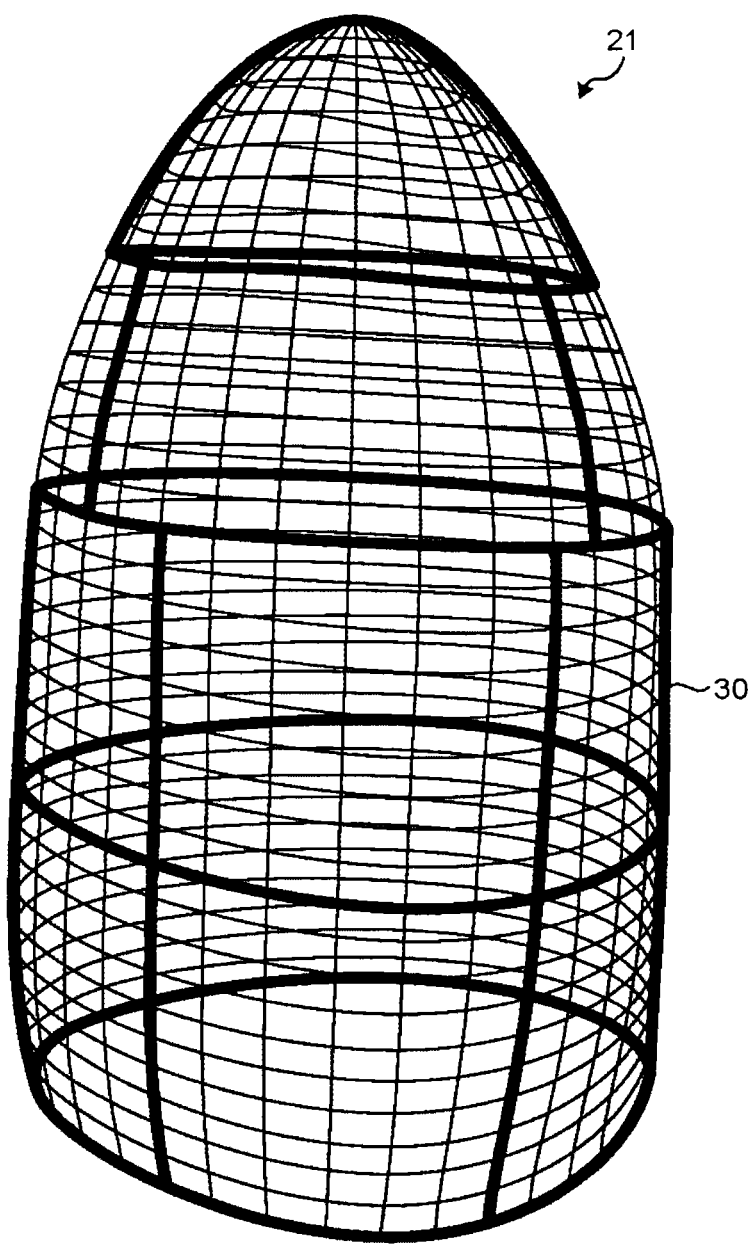
FIG. 3 is a diagram for explaining a region group set by a second setting unit according to the first embodiment.

FIG. 3 is a diagram for explaining the region group set by the second setting unit 175 according to the first embodiment. FIG. 3 illustrates an example of a case in which a region group 30 of the 17-segment model is set on the initial contour 21. The region group 30 is indicated by thick lines in FIG. 3.

As illustrated in FIG. 3, the second setting unit 175 sets the region group 30 of the 17-segment model on the initial contour 21 of the three-dimensional medical image data in which the fixed points are set by the first setting unit 172.

Specifically, the second setting unit 175 divides the initial contour 21 in the long axis direction thereof into four at predetermined address positions. The second setting unit 175 then divides the initial contour 21 divided into four in the circumferential direction thereof at predetermined address positions so as to set the region group 30 constituted by a total of 17 regions (segments). The regions (segments) included in the 17-segment model are adjacent to one another. In other words, each of the regions has boundaries each common to another adjacent region.

The second setting unit 175 also sets indices for identifying respective apexes and boundaries of the regions of interest. For example, in the case of the 17-segment model, a number is set as an index for each of the apexes and the boundaries of the segments. The index is not limited to a number, but only needs to be identification information, such as a character or a symbol, enabling identification of the position of a fixed point. The index is an example of identification information.

In this way, the second setting unit 175 divides the initial contour 21 at the predetermined address positions in the long axis direction and the circumferential direction so as to set each of the apexes of the regions of the region group 30 to any one of the fixed points. The predetermined address positions at which the second setting unit 175 divides the initial contour 21 are set in advance for each segment model (region group) and recorded in a predetermined storage area of the apparatus main unit 100. In other words, the second setting unit 175 sets a boundary of region of interest on the first medical image of the target region according to a position of any one of the fixed points. For example, the boundary on the three-dimensional shape of the target region is set so as to pass through at least one of the fixed points.

The case has been described with reference to FIG. 3 in which the region group 30 of the 17-segment model is set. Embodiments are, however, not limited to this example. For example, in an embodiment, various segment models, such as the 20-segment model and the 7-segment model, may be set, and the regions of interest may have any shape set by the user. The regions of interest need not cover the entire surface of the initial contour 21, and need not include a plurality of regions. That is, the second setting unit 175 may set only one region of interest so as to cover only a part of the initial contour 21. The second setting unit 175 may individually set the regions of interest so as not to be adjacent to one another.

The receiver 176 receives an input entered by the user. For example, the receiver 176 receives, as the entered input, an input to adjust the position of at least either of an apex and a boundary included in a region of interest. The receiver 176 also receives, as the entered input, an input to specify an index. The input is an example of an instruction.

Figure 4:
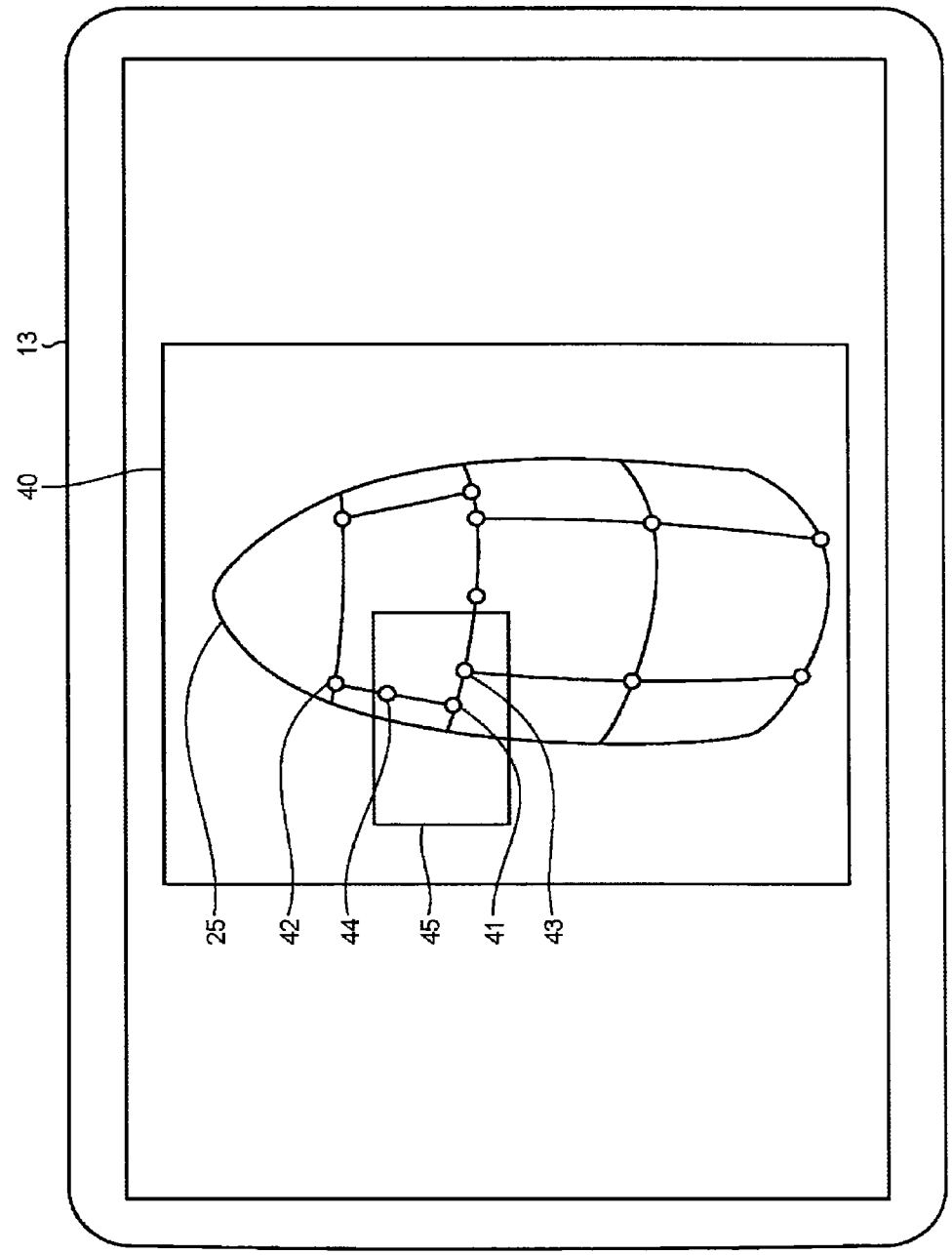
FIG. 4 is a diagram for explaining processing performed by a receiver according to the first embodiment.
Figure 5:
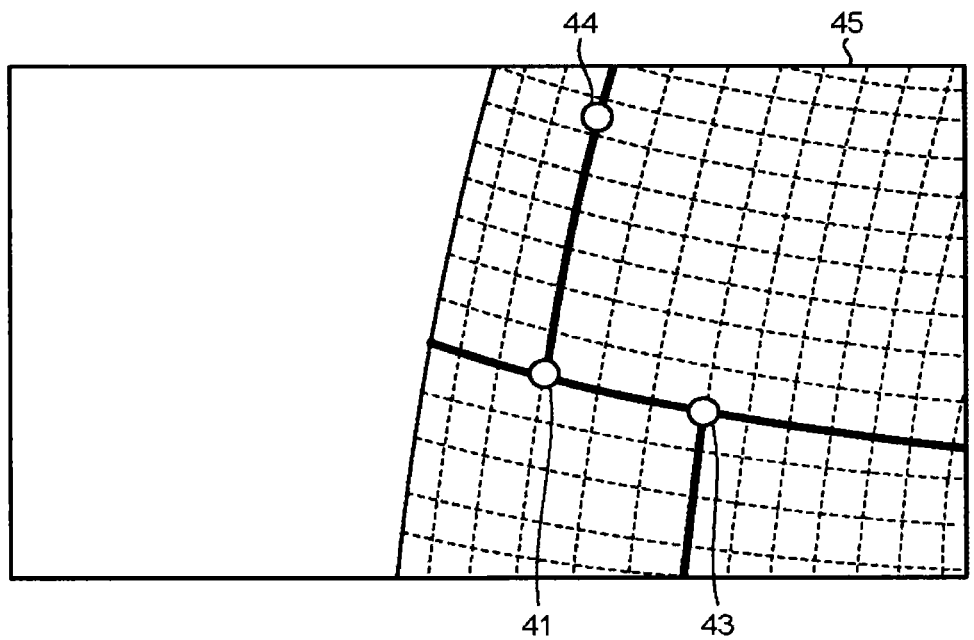
FIG. 5 is a diagram for explaining the processing performed by the receiver according to the first embodiment.

FIGS. 4 and 5 are diagrams for explaining processing performed by the receiver 176 according to the first embodiment. The region of interest serves as an example of the 17-segment model assuming the endocardium surface of the left ventricle. FIG. 4 illustrates an example of a case in which the monitor 13 displays a display region 40 in which an image based on the three-dimensional medical image data is displayed. In FIG. 4, the three-dimensional medical image data displayed in the display region 40 is, for example, a volume rendering image. For example, indices 41, 42, 43, 44, . . . are displayed in the volume rendering image. The indices 41, 42, and 43 are indices for specifying apexes in positions in which the indices are arranged. The index 44 is an index for specifying a boundary in a position in which the index is arranged, that is, a boundary connecting the apex with the index 41 to the apex with the index 42. FIG. 5 corresponds to an enlarged view of a region 45 in FIG. 4. As illustrated in FIG. 5, the respective apexes are set so as to coincide with addresses (fixed points) set on the initial contour 21. As illustrated in FIG. 5, the fixed points and line segments connecting adjacent fixed points are depicted in the rendering image.

As illustrated in FIG. 4, the receiver 176 receives, for example, an input to adjust a boundary of region of interest using the display region 40. The receiver 176 first receives specification of an apex or a boundary to be moved. Specifically, the receiver 176 receives specification of an apex or a boundary to be moved, through the use of one of indices set for the apexes and the boundaries in each segment. For example, if the position of the index 41 is specified by the mouse cursor, the receiver 176 receives information indicating that the apex with the index 41 is specified as an object to be moved. The receiver 176 highlights the specified apex by adjusting, for example, the size, shape, or color thereof.

Then, the receiver 176 receives specification of a moving direction and a moving distance. For example, if the user rotates the mouse wheel upward by a certain amount, the receiver 176 receives information specifying to move the apex with the index 41 upward in the display region 40 by a certain distance. The relation of the operation of the mouse wheel with the moving direction and the moving distance of the apex is set in advance and recorded in a predetermined storage area of the apparatus main unit 100.

In this way, the receiver 176 receives the input to adjust the boundary of the region of interest set on the initial contour 21. The receiver 176 then outputs the received information, such as the position, the moving direction, and the moving distance of the apex or boundary to be moved, to the adjuster 177. Although not described with reference to FIG. 4, the receiver 176 receives a specification indicating that a boundary is to be moved in the same way as the apex, and also receives a specification of a moving direction and a moving distance. In other words, the receiver 176 receives an instruction to change the position of the boundary from the input device (input unit 12) operated by the user.

The case has been described with reference to FIG. 4 in which various inputs are made by the mouse operation. Embodiments are, however, not limited to this example. For example, the receiver 176 can receive various inputs through operations of various input devices, such as a pointing device other than the mouse, a keyboard, a foot switch, a touch screen, and a graphics tablet. For example, if the apex with the index 41 is associated with the "1" key of the keyboard, pressing the "1" key of the keyboard may cause the receiver 176 to receive information specifying the apex with the index 41 as an object to be moved. Pressing the up-arrow key may cause the receiver 176 to receive information specifying an upward movement. In this case, for example, the moving distance is set in advance corresponding to the number of times of depression of the key. If the touch screen is used, a touch may cause the receiver 176 to receive the specification of the object to be moved, and a swipe or a flick may cause the receiver 176 to receive the specification of the moving direction and the moving distance.

The above has described with reference to FIG. 4 that an apex or a boundary specified to be moved is highlighted. Embodiments are, however, not limited to this example. That is, the object to be moved need not be highlighted. Also, for example, the object to be moved, the moving direction, and the moving distance may be specified by only operation of the mouse cursor, without the use of the index.

After the receiver 176 receives the input, the adjuster 177 adjusts the boundary of the region of interest with respect to positions for which the identification information has been set. For example, the adjuster 177 adjusts the boundary of the region of interest so that the apex, or an apex included in the boundary, to be adjusted in position by the input coincides with any of the fixed points.

FIGS. 6 and 7 are diagrams for explaining processing performed by the adjuster 177 according to the first embodiment. FIG. 6 illustrates an example of a case in which the apex with the index 41 is moved upward. FIG. 7 illustrates an example of a case in which the boundary with the index 44 is moved rightward. In FIGS. 6 and 7, the position of a fixed point in any frame "t" is represented as two-dimensional information (h,d).

As illustrated in the left diagram of FIG. 6, if, for example, the apex with the index 41 is specified, movable directions of the specified apex are displayed near the apex. If the apex is movable in the up-down direction, arrows in the up and down directions are displayed above and below the apex, respectively (guide display), as illustrated in the left diagram of FIG. 6. If an instruction is made to move the apex upward by a certain distance, the apex with the index 41 is moved upward by the certain distance, as illustrated in the right diagram of FIG. 6.

In this case, the adjuster 177 adjusts the position of the apex to be moved according to the specification of the moving direction and the moving distance. For example, the adjuster 177 receives, from the receiver 176, the position (h1,d1), and the moving direction and the moving distance "+20", of the apex to be moved. The moving direction and the moving distance "+20" indicate that the apex is to be moved upward in FIG. 6 by a distance of 20 addresses. In this case, the adjuster 177 adds 20 to the coordinate value in the long axis direction of the apex to be moved, and moves the position of the apex to (h1+20,d1). The adjuster 177 also calculates shortest paths between the apex after being moved and apexes adjacent thereto. In this case, the adjuster 177 obtains, for example, paths that are shortest between the apex after being moved and apexes adjacent thereto and that run on the initial contour 21. In the example illustrated in FIG. 6, the adjuster 177 obtains the shortest path between the apex with the index 41 and the apex with the index 42, and also obtains the shortest path between the apex with the index 41 and the apex with the index 43. Then, the adjuster 177 draws a boundary passing through the obtained shortest paths so as to adjust the segments of the region group 30. In the example of FIG. 6, moving the apex with the index 41 upward changes the shape of the region of interest. Specifically, shortening the boundary with the index 44 changes the shape of the region of interest with the left side serving as the boundary from quadrilateral to pentagonal. In other words, the point with the index 43 is not an apex of the region of interest before the movement, but becomes a new apex after the movement, so that the region of interest becomes quadrilateral. In this way, adjusting the boundary of the region of interest increases the apexes of the region of interest in some cases.

As illustrated in the left diagram of FIG. 7, if, for example, the boundary with the index 44 is specified, movable directions of the specified boundary are displayed near the boundary. If the boundary is movable in the right-left direction, arrows in the right and left directions are displayed on the right and left of the boundary, respectively (guide display), as illustrated in the left diagram of FIG. 7. If an instruction is made to move the boundary rightward by a certain distance, the boundary with the index 44 is moved rightward by the certain distance, as illustrated in the right diagram of FIG. 7.

In this case, the adjuster 177 adjusts the position of the boundary to be moved according to the specification of the moving direction and the moving distance. For example, the adjuster 177 receives, from the receiver 176, the positions (h1,d1) and (h2,d2), and the moving direction and the moving distance "+15", of two apexes included in the boundary to be moved. The position (h1,d1) corresponds to the position of the apex with the index 41, and the position (h2,d2) corresponds to the position of the apex with the index 42. The moving direction and the moving distance "+15" indicate that the apexes are to be moved rightward in FIG. 7 by a distance of 15 addresses. In this case, the adjuster 177 adds 15 to the coordinate values in the circumferential direction of the apexes included in the boundary to be moved, and moves the positions of the apexes to (h1, d1+15) and (h2,d2+15). The adjuster 177 also calculates paths that are shortest between the apexes of the boundary after being moved and apexes adjacent thereto and that run on the initial contour 21. In the example illustrated in FIG. 7, the adjuster 177 obtains, for example, the shortest path between the apex with the index 41 and the apex with the index 43. Then, the adjuster 177 draws a boundary passing through the obtained shortest paths so as to adjust the segments of the region group 30.

In this way, after the receiver 176 receives the input, the adjuster 177 adjusts the boundary of the region of interest with respect to the fixed points. Then, the adjuster 177 outputs the three-dimensional medical image data with the adjusted region of interest to the display controller 178. In other words, the adjuster 177 changes the position of the boundary based on a position or positions of at least one of the fixed points according to the instruction from the user while maintaining the positions of the fixed points. For example, the boundary is changed so that the changed boundary passes through at least one of the fixed points that the previous boundary does not pass through.

As described with reference to FIGS. 6 and 7, movable directions of each of the apexes and the boundaries are set in advance. For example, the long axis direction, the circumferential direction, and a combination of, for example, the long axis direction and the circumferential direction are set in advance as movable directions, and are stored in a predetermined storage area of the apparatus main unit 100. This setting can prevent each of the apexes and the boundaries from being adjusted to an unnatural position, and allows the movement of each of the apexes and the boundaries to be specified by simple operations.

FIGS. 6 and 7 merely illustrate examples. The user can freely adjust any of the apexes and the boundaries. The cases have been described with reference to FIGS. 6 and 7 in which the apex moves in the long axis direction or the circumferential direction. Embodiments are, however, not limited to this example. For example, the apex to be moved may be configured to move along the boundary including the apex. That is, the apex or an apex included in the boundary need not be moved along the long axis direction or the circumferential direction.

With reference to FIGS. 6 and 7, the typical examples have been described of the cases in which the apex and the boundary are adjusted. Embodiments are, however, not limited to these examples. For example, the embodiments are applicable to a case in which a boundary around a full circle is specified as an object to be moved. For example, in FIG. 7, a boundary including the index 42 around a full circle in the circumferential direction is specified as an object to be moved. In this case, the region of interest surrounded by the boundary including the index 42 is a cap-like region including the cardiac apex of the left ventricle. The boundary including the index 42 is moved downward.

Specifically, the adjuster 177 adjusts the position of the point (index 42) on the boundary to be moved, according to the specification of the moving direction and the moving distance. For example, the adjuster 177 receives, from the receiver 176, the position (h2,d2), and the moving direction and the moving distance "−5", of the point (index 42) included in the boundary to be moved. The moving direction and the moving distance "−5" indicate that the point is to be moved downward in FIG. 7 by a distance of 5 addresses. In this case, the adjuster 177 subtracts 5 from the coordinate value in the long axis direction of the point on the boundary to be moved, and moves the position of the point to (h2−5,d2). Then, the adjuster 177 sets a line in the circumferential direction passing through the point after the movement to be a boundary so as to adjust the cap-like region of interest. In this way, in the case of moving a boundary around a full circle, the adjuster 177 adjusts the position of a point on the boundary. That is, what can be specified and adjusted as an object to be moved is not limited to an apex or a boundary, but only needs to be a point on a boundary of region of interest.

The display controller 178 controls the monitor 13 to display images based on the three-dimensional medical image data including the region of interest. For example, each time the adjuster 177 adjusts the boundary of the region of interest, the display controller 178 controls the monitor 13 to display at least either of any cross-sectional image and the volume rendering image, based on the three-dimensional medical image data including the region of interest after the adjustment.

Figure 8:
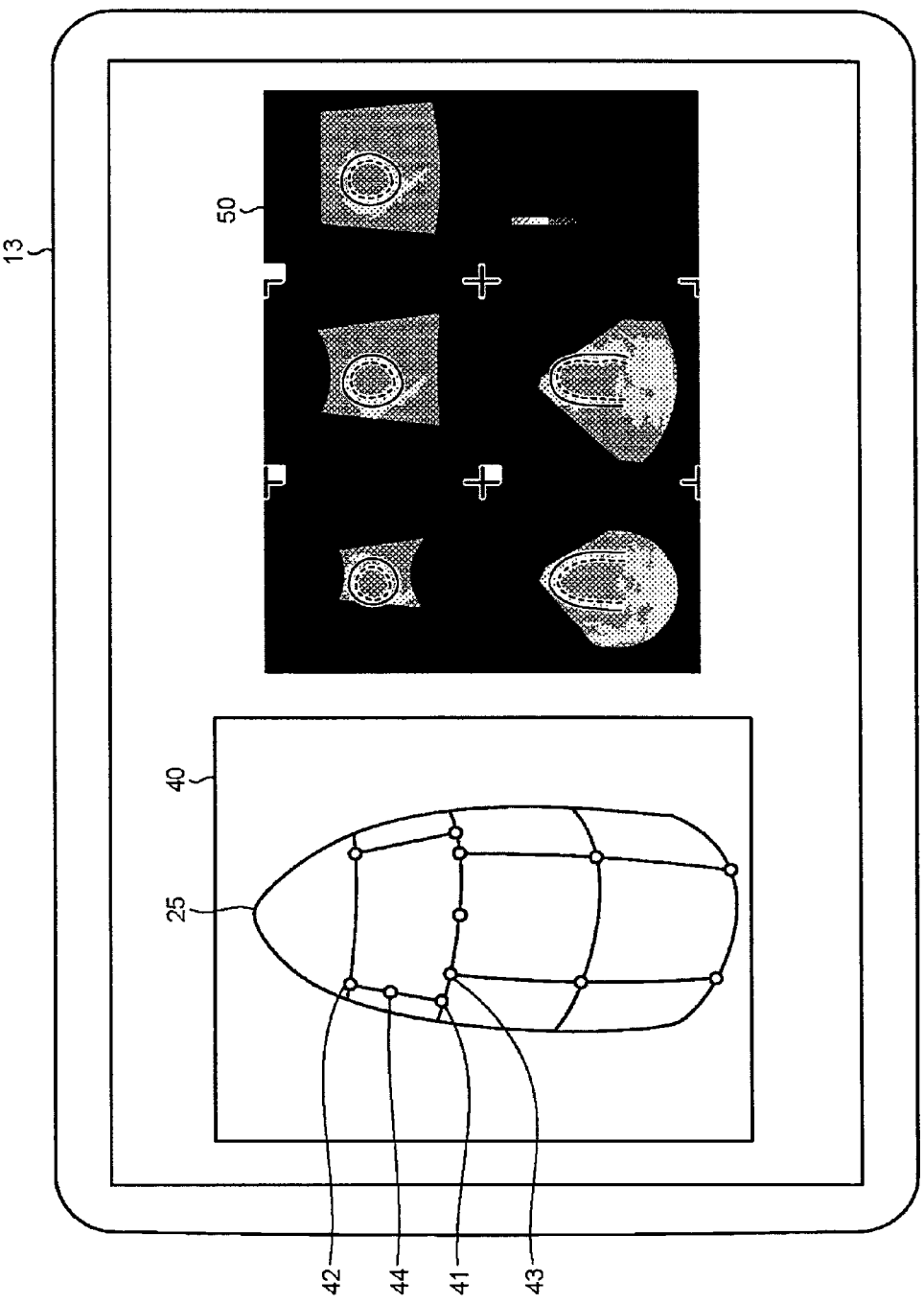
FIG. 8 is a diagram illustrating an example of images displayed by a display controller according to the first embodiment.

FIG. 8 is a diagram illustrating an example of images displayed by the display controller 178 according to the first embodiment. FIG. 8 illustrates an example of a case in which the monitor 13 displays in parallel the display region 40 and a display region 50 that display the images based on the three-dimensional medical image data. The display region 40 displays the same volume rendering image as that illustrated in FIG. 4. The display region 50 displays a cross-sectional image based on the three-dimensional medical image data. This cross-sectional image is an image including short axis cross-sections and long axis cross-sections in certain positions, and depicts positions (dashed-lined portions) corresponding to the endocardium of the heart and positions (solid-lined portions) corresponding to the epicardium of the heart.

As illustrated in FIG. 8, the display controller 178 receives, for example, the three-dimensional medical image data with the adjusted region of interest from the adjuster 177. The display controller 178 then controls the image generator 140 to generate the image for display based on the three-dimensional medical image data with the adjusted region of interest. In FIG. 8, the display controller 178 controls the image generator 140 to generate the image for display that depicts in parallel the display region 40 with the volume rendering image displayed therein and the display region 50 with the cross-sectional image displayed therein.

The display controller 178 then controls the monitor 13 to display the image for display generated by the image generator 140.

In this way, the display controller 178 controls the monitor 13 to display the images based on the three-dimensional medical image data including the region of interest. FIG. 8 illustrates the case in which the cross-sectional image and the volume rendering image are displayed in parallel. Embodiments are, however, not limited to this example. For example, the case in an embodiment may be such that only one of these images is displayed. The display controller 178 may also control the monitor 13 to display other information, such as a polar map. In other words, before the position of the boundary of the region of interest is changed, the display controller 178 controls the display unit to display a first rendering image obtained by applying the rendering processing to three-dimensional image data representing a part of the three-dimensional shape of the target region and the region of interest before the position of the boundary is changed, and after the position of the boundary of the region of interest is changed, the display controller 178 controls the display unit to display a second rendering image obtained by applying the rendering processing to three-dimensional image data representing the part of the three-dimensional shape of the target region and the region of interest after the position of the boundary is changed. For example, the receiver 176 receives an instruction with respect to the first rendering image displayed on the display unit.

Figures 9, 10:
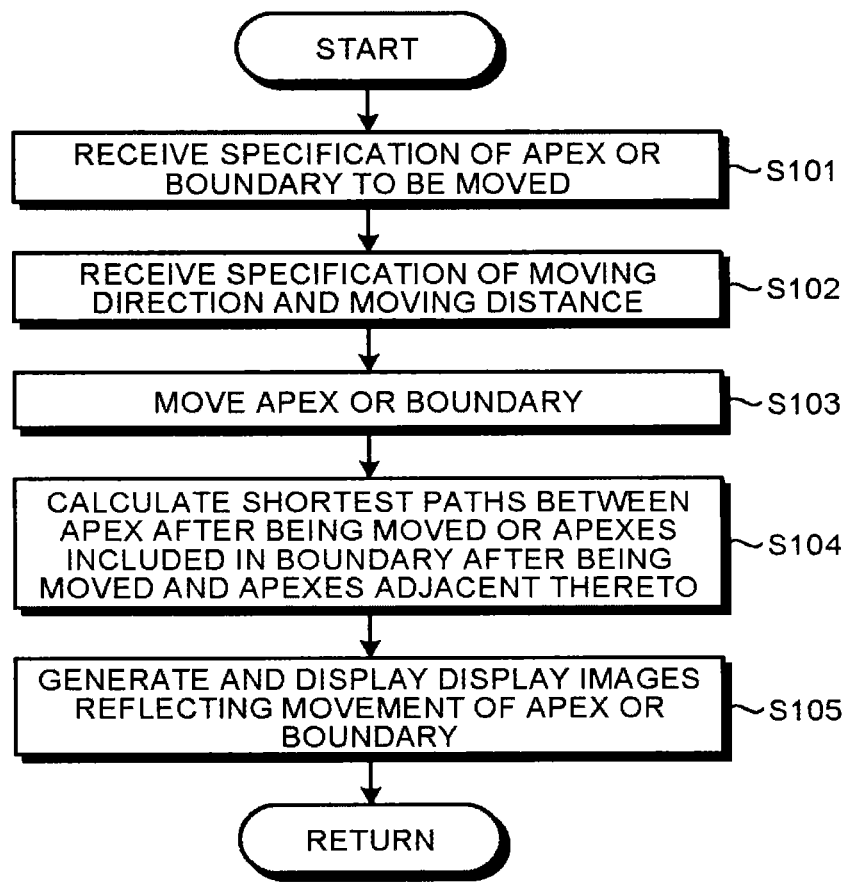
FIG. 9 is a flowchart for explaining processing for adjusting a boundary according to the first embodiment.
FIG. 10 is a diagram for explaining processing performed by a second setting unit according to a first modification of the first embodiment.

The following describes processing for adjusting the boundary according to the first embodiment. FIG. 9 is a flowchart for explaining the processing for adjusting the boundary according to the first embodiment. FIG. 9 explains a case in which the processing by the first and second setting units 172 and 175 has been completed, and the monitor 13 displays the image for display before being adjusted (corresponding to the left diagram of FIG. 6).

As illustrated in FIG. 9, the receiver 176 of the ultrasonic diagnostic apparatus 1 receives specification of an apex or a boundary to be moved (Step S101). For example, the receiver 176 receives specification of an apex or a boundary to be moved provided by operation of the mouse cursor, through the use of one of indices set for the apexes and the boundaries in each segment of the segment model. The receiver 176 subsequently receives specification of a moving direction and a moving distance (Step S102). For example, if the user rotates the mouse wheel upward by a certain amount, the receiver 176 receives information specifying to move the apex with the index 41 upward in the display region 40 by a certain distance.

Then, the adjuster 177 moves the apex or the boundary (Step S103). For example, the adjuster 177 receives the moving direction and the moving distance from the receiver 176, and calculates the position of the apex after being moved based on the received information. The adjuster 177 subsequently calculates shortest paths between the apex after being moved or apexes included in the boundary after being moved and apexes adjacent thereto (Step S104). The adjuster 177 obtains, for example, paths that are shortest between the apex after being moved and apexes adjacent thereto and that run on the initial contour 21. The adjuster 177 then draws a boundary passing through the obtained shortest paths so as to adjust the segments of the region group 30.

Then, the display controller 178 performs control to generate and display images reflecting the movement of the apex or the boundary (Step S105). For example, the display controller 178 performs control to generate any images for display, such as the cross-sectional image and the volume rendering image, based on the three-dimensional medical image data with the region of interest adjusted, and to display the generated images on the monitor 13.

In this way, the ultrasonic diagnostic apparatus 1 according to the first embodiment adjusts the boundary of the region of interest set on the surface of the heart according to the control of the input device by the user.

As has been described above, the ultrasonic diagnostic apparatus 1 according to the first embodiment sets apexes forming the region of interest established on the surface of the heart for analyzing the surface thereof at the fixed points on the surface of the heart. When adjusting the boundary of the region of interest, the ultrasonic diagnostic apparatus 1 adjusts the boundary with respect to the fixed points. This allows the ultrasonic diagnostic apparatus 1 according to the first embodiment to easily adjust the boundary of the region of interest in the three-dimensional image. As a result, the ultrasonic diagnostic apparatus 1 can, for example, reduce time required for analysis and diagnosis, and improve accuracy of the analysis and the diagnosis. The standard segment models of the left ventricle are intended to correspond to a region dominated by coronary arteries, so that the boundary needs to be adjusted in some individual cases. No standard segment model is available for heart chambers (the left atrium, the right ventricle, and the right atrium) other than the left ventricle, so that cases increase that require adjustment of the boundary as a way of setting a region of interest to be observed. The present application increases the effects described above in those cases.

In the first embodiment, the case has been described in which the ultrasonic diagnostic apparatus 1 calculates the motion information of the heart wall by performing the cardiac wall motion tracking using the three-dimensional image processing. The motion information need not, however, be calculated. That is, the ultrasonic diagnostic apparatus 1 according to the first embodiment need not include the tracker 173 and the motion information calculator 174.

That is, the ultrasonic diagnostic apparatus 1 according to the first embodiment only needs to include the acquiring unit 171, the first setting unit 172, the second setting unit 175, the receiver 176, the adjuster 177, and the display controller 178. For example, the acquiring unit 171 acquires the three-dimensional medical image data obtained by photographing at least a part of the heart. The first setting unit 172 sets the identification information for identifying each position among positions corresponding to the surface of the heart in the three-dimensional medical image data. The second setting unit 175 sets the apexes forming the region of interest in the positions for which the identification information has been set. The receiver 176 receives the input to adjust the boundary of the region of interest. After the receiver 176 receives the input, the adjuster 177 adjusts the boundary of the region of interest with respect to the positions for which the identification information has been set. The display controller 178 controls the display unit to display the images based on the three-dimensional medical image data including the region of interest. In this way, the ultrasonic diagnostic apparatus 1 can easily adjust the boundary of the region of interest in the three-dimensional image.

First Modification of First Embodiment

In the first embodiment described above, the second setting unit 175 may further set a region of interest according to a photographed region of the heart in the three-dimensional medical image data.

FIG. 10 is a diagram for explaining processing performed by the second setting unit 175 according to a first modification of the first embodiment. FIG. 10 illustrates an example of a table referred to by the second setting unit 175. This table is stored in advance as setting information in a predetermined storage area of the apparatus main unit 100.

As illustrated in FIG. 10, the table stores information associating each region of the heart with a segment pattern. The "region of heart" is information indicating the photographed region of the heart in the three-dimensional medical image data. The "segment pattern" is information representing a segment model corresponding to the region of the heart.

In this case, the second setting unit 175 sets a segment model according to the photographed region of the heart in the three-dimensional medical image data. For example, the second setting unit 175 performs pattern recognition on the three-dimensional medical image data to be processed against teacher data (dictionary data) for respective regions of the heart, and thereby determines which of, for example, the left ventricle and the left atrium corresponds to the region of the heart included in the three-dimensional medical image data. The second setting unit 175 then selects a segment model corresponding to the determined region of the heart, with reference to the table of FIG. 10. The second setting unit 175 then sets the selected segment model.

In this way, the second setting unit 175 sets the region of interest according to the photographed region of the heart in the three-dimensional medical image data. Through this operation, the ultrasonic diagnostic apparatus 1 can automatically set an appropriate segment model for each region to be processed.

The above example has been described of the case of performing the pattern recognition. Embodiments are, however, not limited to this example. For example, the second setting unit 175 may refer to information mentioned in an electronic medical record of the subject, and set the region of interest based on the information. If, for example, the electronic medical record mentions "right ventricle", the second setting unit 175 sets the 7-segment model corresponding to the right ventricle, with reference to the table of FIG. 10.

Second Modification of First Embodiment

For example, the polar map may be used to receive the adjustment of the boundary of the region of interest.

Figure 11:
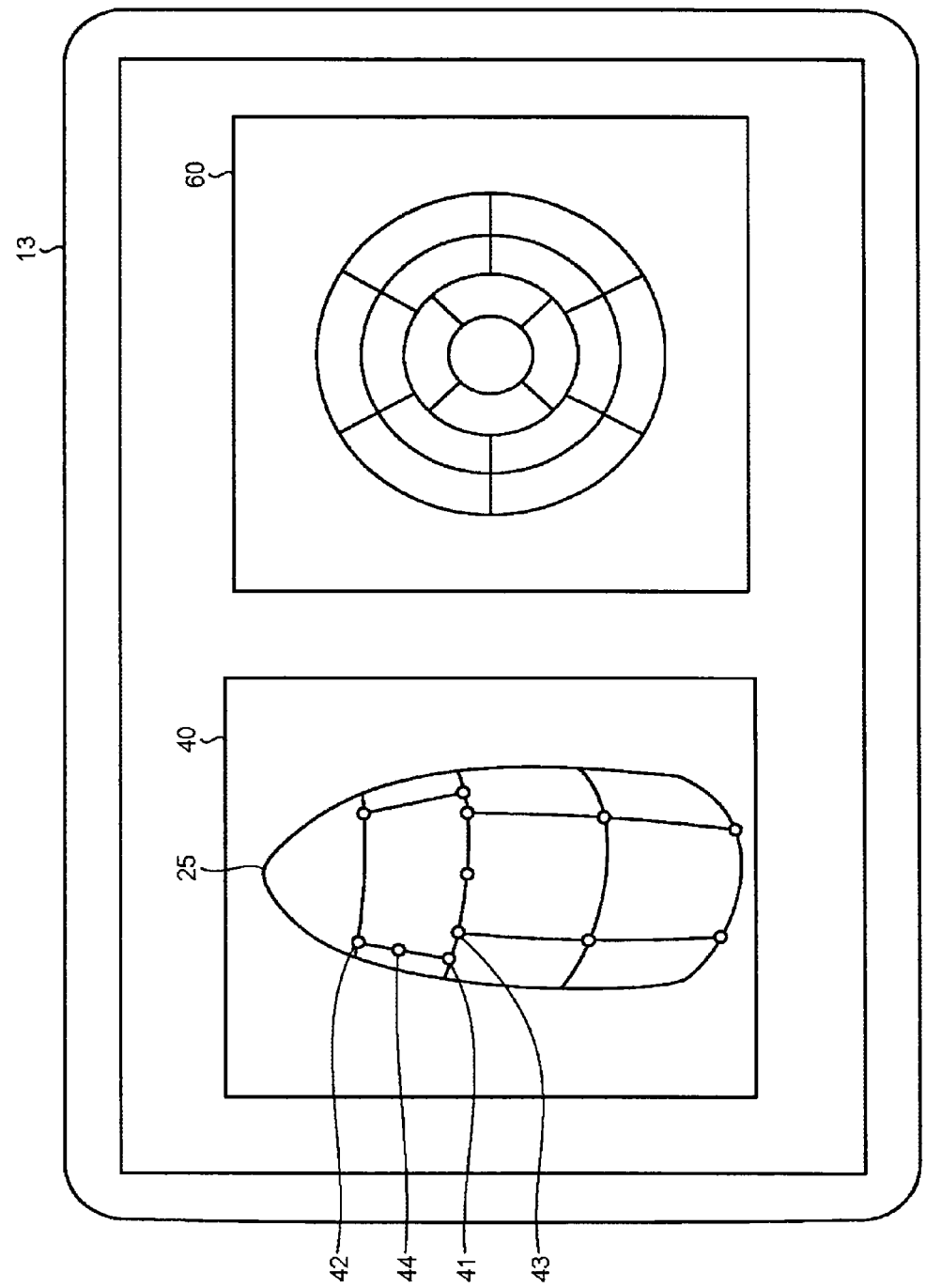
FIG. 11 is a diagram for explaining processing performed by a receiver according to a second modification of the first embodiment.

FIG. 11 is a diagram for explaining processing performed by the receiver 176 according to a second modification of the first embodiment. FIG. 11 illustrates an example of a case of displaying in parallel the display region 40 that displays an image based on the three-dimensional medical image data and a display region 60 that displays the polar map. The display region 40 displays the same volume rendering image as that illustrated in FIG. 4. The display region 60 displays the polar map of the heart associated with the segment model (region of interest) set in the three-dimensional medical image data displayed in the display region 40.

For example, as illustrated in FIG. 11, the display controller 178 controls the monitor 13 to display the polar map of the heart associated with the segment model (region of interest). Specifically, the display controller 178 generates the polar map corresponding to the segment model (such as the 17-segment model) set on the initial contour 21. The apexes and the boundaries on the polar map are associated with the apexes and the boundaries of the segment model set on the initial contour 21.

According to control applied to an apex or a boundary on the polar map displayed on the monitor 13, the receiver 176 receives adjustment of position information of an apex or a boundary corresponding to the apex or the boundary on the polar map. If, for example, any of the apexes and the boundaries in the display region 60 is specified by the mouse cursor, the receiver 176 receives information indicating that the apex with the index 41 is specified as an object to be moved. Then, if, for example, the user rotates the mouse wheel by a certain amount in a certain direction, the receiver 176 receives information specifying to move the specified apex or boundary by a certain distance in the certain direction. The receiver 176 outputs various types of information received to the adjuster 177 so as to control the adjuster 177 to adjust the apexes and the boundaries, as described above. As a result, for example, the apexes and the boundaries in the display region 40 are adjusted.

In the example of FIG. 11, the positions of the apexes and the positions of the boundaries on the polar map displayed in the display region 60 are preferably not adjusted. That is, the polar map in the display region 60 is displayed to receive the adjustment of the position information of the apex or the boundary. This allows the user to enter the adjustment of the apex or the boundary in the volume rendering image displayed in parallel with the polar map, in the condition where the polar map is always displayed unchanged.

However, not limited to this, the positions of the apexes and the positions of the boundaries on the polar map displayed in the display region 60 may be adjusted as the position information thereof is adjusted. FIG. 11 illustrates the case of parallel display. However, not limited to this case, the display region 40 or the display region 60 may be individually displayed.

Second Embodiment

In a second embodiment, a case will be described in which, each time the boundary of the region of interest is adjusted, the ultrasonic diagnostic apparatus 1 further calculates an indicator value indicating the motion information of the fixed points included in the region of interest after the adjustment, and presents the calculated indicator value to the user.

Figure 12:
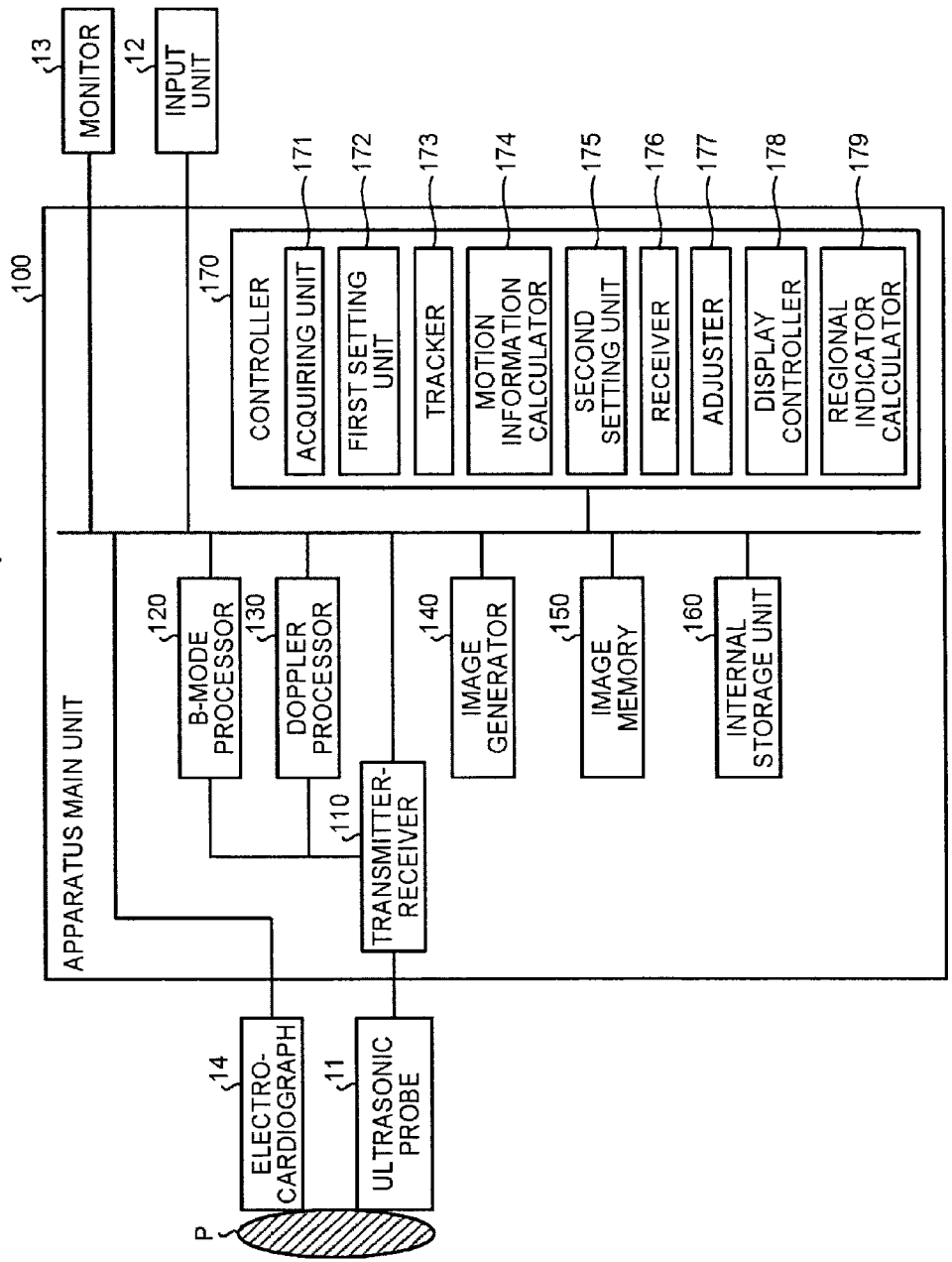
FIG. 12 is a block diagram illustrating a configuration example of the ultrasonic diagnostic apparatus according to a second embodiment.

FIG. 12 is a block diagram illustrating a configuration example of the ultrasonic diagnostic apparatus 1 according to the second embodiment. As illustrated in FIG. 12, the ultrasonic diagnostic apparatus 1 according to the second embodiment differs from the ultrasonic diagnostic apparatus 1 illustrated in FIG. 1 in including a regional indicator calculator 179 and in a part of the processing in the display controller 178. Hence, in the second embodiment, only differences from the first embodiment will be described, and the same points will not be described.

Each time the region of interest is adjusted, the regional indicator calculator 179 calculates a value (indicator value) indicating the motion information of the positions included in the region of interest after the adjustment. For example, each time a boundary of any region among regions included in the segment model is adjusted, the regional indicator calculator 179 calculates the indicator value based on the motion information of the fixed points included in the region including the adjusted boundary. The indicator value is, for example, a mean value, a variance, or a standard deviation, but may be any indicator value predefined by the user.

The display controller 178 controls the monitor 13 to display the indicator value, each time the regional indicator calculator 179 calculates the indicator value. For example, according to the level of the indicator value calculated by the regional indicator calculator 179, the display controller 178 changes the pixel value of the region for which the indicator value has been calculated.

FIG. 13 is a diagram for explaining processing performed by the display controller 178 according to the second embodiment. The left diagram of FIG. 13 illustrates an example of the volume rendering image before the boundary is adjusted. The right diagram of FIG. 13 illustrates an example of the volume rendering image after the boundary is adjusted.

As illustrated in the left diagram of FIG. 13, a region 70 of the segment model is assigned with a certain pixel value. This pixel value corresponds to the level of the value calculated by the regional indicator calculator 179 based on the motion information of the fixed points included in the region 70.

If, for example, the apex with the index 41 is moved upward, the shape of the region 70 is adjusted as illustrated in the right diagram of FIG. 13. This adjustment causes the regional indicator calculator 179 to calculate the indicator value based on the motion information of the fixed points included in the region of interest after the adjustment, as described above. After the regional indicator calculator 179 calculates the index value, the display controller 178 assigns the region 70 with the pixel value corresponding to the level of the calculated value, and generates the display region 40. Hence, in the example of FIG. 13, the region 70 after the boundary adjustment is displayed in a darker color.

In this way, the display controller 178 controls the monitor 13 to display the region with the pixel value corresponding to the indicator value, each time the regional indicator calculator 179 calculates the indicator value for the region.

The case has been described with reference to FIG. 13 in which the indicator value for the region after the boundary adjustment is reflected to the pixel value of the region. Embodiments are, however, not limited to this example. For example, the display controller 178 may perform control to display the calculated indicator value by superimposing it as text information in the display region 40. If the indicator value is calculated as a value changing with time, the value may be displayed, for example, as a graph with the horizontal axis representing time. In other words, the display controller 178 controls the display unit to display the motion information for the region of interest in a predetermined display form.

In this way, each time the boundary of the region of interest is adjusted, the ultrasonic diagnostic apparatus 1 according to the second embodiment calculates the indicator value indicating the motion information of the fixed points included in the region of interest after the adjustment, and presents the calculated indicator value to the user. This presentation allows the user to immediately view the change in the indicator value according to the adjustment of the boundary on the monitor 13. This is expected to allow a user to, for example, improve accuracy in setting of the region of interest and in analysis results by, for example, adjusting the boundary to that giving an appropriate calculated indicator value.

The various modifications described above in the first embodiment are also applicable to the second embodiment unless any contradiction occurs in the details of processing.

Other Embodiments

While the first and second embodiments have been described, various different embodiments may be employed in addition to the embodiments described above.

Application to Image Processing Apparatus

For example, the functions described in the first and second embodiments are applicable not only to the medical diagnostic imaging apparatus (medical diagnosis apparatus), but also to the image processing apparatus.

Figure 14:
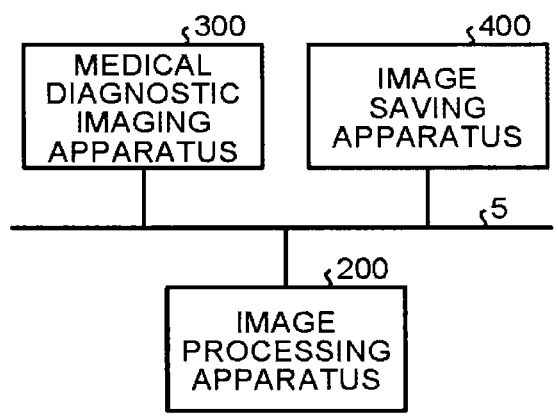
FIG. 14 is a diagram illustrating a configuration example of an image processing system according to another embodiment.

FIG. 14 is a diagram illustrating a configuration example of an image processing system according to another embodiment. As illustrated in FIG. 14, the image processing system according to the other embodiment includes an image processing apparatus 200, a medical diagnostic imaging apparatus 300, and an image saving apparatus 400. The apparatuses illustrated in FIG. 14 are directly or indirectly communicable with one another through, for example, an in-house local area network (LAN) 5 installed in a hospital. For example, if a picture archiving and communication system (PACS) is introduced, the apparatuses send and receive, for example, the medical image data between one another according to the Digital Imaging and Communications in Medicine (DICOM) standard.

In FIG. 14, for example, the medical diagnostic imaging apparatus 300 captures the three-dimensional medical image data, and stores the captured three-dimensional medical image data in the image saving apparatus 400. The medical diagnostic imaging apparatus 300 corresponds to, for example, the ultrasonic diagnostic apparatus, the X-ray diagnostic apparatus, the X-ray computed tomography (CT) apparatus, the magnetic resonance imaging (MRI) apparatus, the single-photon emission computed tomography (SPECT) apparatus, the positron emission tomography (PET) apparatus, the SPECT-CT apparatus obtained by integrating the SPECT apparatus with the X-ray CT apparatus, the PET-CT apparatus obtained by integrating the PET apparatus with the X-ray CT apparatus, the PET-MRI apparatus obtained by integrating the PET apparatus with the MRI apparatus, or an apparatus group including more than one of these apparatuses. For example, the medical diagnostic imaging apparatus 300 includes at least a scanner. The scanner scans a three-dimensional region including a target region and acquires data of the three-dimensional region. The ultrasonic diagnostic apparatus includes at least an ultrasonic probe as the scanner. Each of the X-ray diagnostic apparatus and the X-ray CT apparatus includes at least an X-ray tube and an X-ray detector as the scanner. The MRI apparatus includes at least various types of coils as the scanner. Each of the SPECT apparatus and the PET apparatus includes at least a detector as the scanner.

The image saving apparatus 400 is a database for saving the medical image data. Specifically, the image saving apparatus 400 stores and saves the three-dimensional medical image data generated by one of the various types of the medical diagnostic imaging apparatus 300 into a storage unit of the image saving apparatus 400. The three-dimensional medical image data is saved in the image saving apparatus 400 in a manner associated with supplementary information, such as the patient ID, a test ID, an apparatus ID, and a series ID.

The image processing apparatus 200 is, for example, a workstation or a personal computer (PC) used for viewing medical images by a doctor or a medical technologist working in a hospital. The user of the image processing apparatus 200 performs search using the patient ID, the test ID, the apparatus ID, the series ID, and the like so as to obtain necessary three-dimensional medical image data from the image saving apparatus 400. Alternatively, the image processing apparatus 200 may directly receive the three-dimensional medical image data from the medical diagnostic imaging apparatus 300.

Figure 15:
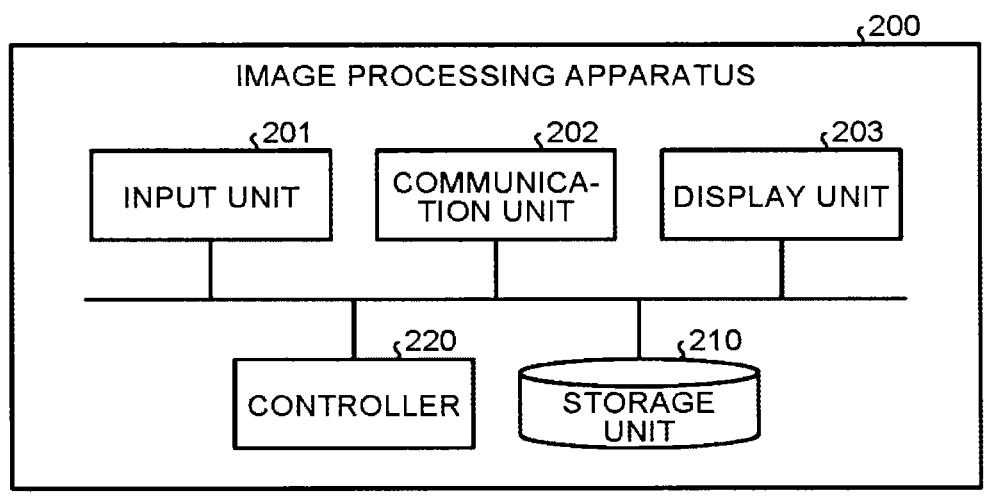
FIG. 15 is a diagram illustrating a configuration example of an image processing apparatus according to the other embodiment.

FIG. 15 is a diagram illustrating a configuration example of the image processing apparatus 200 according to the other embodiment. As illustrated in FIG. 15, the image processing apparatus 200 includes an input unit 201, a communication unit 202, a display unit 203, a storage unit 210, and a controller 220. The input unit 201, the communication unit 202, the display unit 203, the storage unit 210, and the controller 220 are connected to one another.

The input unit 201 is, for example, the pointing device, such as the mouse or the graphics tablet, the keyboard, and the track ball, and receives various types of control input for the image processing apparatus 200 from the user. If the mouse is used, the mouse wheel can be used for the input. If the graphics tablet is used, a flick operation and a swipe operation can be used for the input. The communication unit 202 is, for example, a network interface card (NIC), and communicates with other apparatuses. The display unit 203 is, for example, the monitor or a liquid crystal panel, and displays various types of information.

The storage unit 210 is, for example, a hard disk or a semiconductor memory device, and stores various types of information. The storage unit 210 stores, for example, a plurality of processes executed by the controller 220.

The controller 220 is, for example, an electronic circuit, such as a central processing unit (CPU) or a micro processing unit (MPU), or an integrated circuit, such as an application specific integrated circuit (ASIC) or a field programmable gate array (FPGA), and performs overall control of the image processing apparatus 200.

The controller 220 includes the same processing units as the acquiring unit 171, the first setting unit 172, the second setting unit 175, the receiver 176, the adjuster 177, and the display controller 178. That is, the same processing unit as the acquiring unit 171 acquires the three-dimensional medical image data obtained by photographing at least a part of the heart; the same processing unit as the first setting unit 172 sets the identification information for identifying each position among positions corresponding to the surface of the heart in the three-dimensional medical image data; the same processing unit as the second setting unit 175 sets points on the boundary of region of interest in positions for which the identification information has been set; the same processing unit as the receiver 176 receives the input to adjust the boundary of the region of interest; after the receiver 176 receives the input, the same processing unit as the adjuster 177 adjusts the boundary of the region of interest with respect to the positions for which the identification information has been set; and the same processing unit as the display controller 178 controls the display unit to display the images based on the three-dimensional medical image data including the region of interest. In this way, the image processing apparatus 200 can easily adjust the boundary of the region of interest in the three-dimensional image.

For example, the components of the respective apparatuses illustrated in the drawings in the embodiments described above are based on the functional concept, and not necessarily physically configured as illustrated in the drawings. That is, the specific forms of distribution and integration of the apparatuses are not limited to those illustrated in the drawings, and all or some of the apparatuses can be configured by being functionally or physically distributed or integrated in any units according to various loads, use conditions, and the like. Furthermore, all or any number of processing functions performed in the respective apparatuses can be carried out by a CPU and a program analyzed and executed by the CPU, or can be implemented as hardware by wired logic.

The method for image processing described above may be applied not only to the heart, but also to organs, such as the lungs or the liver.

In one of the embodiments described above, the case has been described in which the embodiment is applied to the wall motion tracking (WMT). Embodiments are, however, not limited to this case. That is, the embodiments herein are widely applicable to cases of adjusting the boundary of the region of interest set on a surface of a subject included in the volume data. The surface of the subject may be a surface (contour) of an organ of the subject, or a body surface of the subject. In this case, any conventional technology may be used to detect the surface of the subject.

The method for image processing described in the embodiments and the modifications thereof given above can be carried out by executing a prepared image processing program on a computer, such as a personal computer or a workstation. The image processing program can be distributed through a network, such as the Internet. The image processing program can also be executed by being recorded in a computer-readable recording medium, such as a hard disk, a flexible disk (FD), a CD-ROM, an MO, and a DVD, and by being read from the recording medium by the computer.

According to at least one of the embodiments described above, a boundary of region of interest in a three-dimensional image can be easily adjusted.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnosis apparatus comprising:
a scanner configured to scan a three-dimensional region including a target region and acquire data of the three-dimensional region; and
processing circuitry configured to:
generate a first three-dimensional medical image based on the data;
discretely arrange fixed points framing a first region of interest (ROI) corresponding to the target region in the first three-dimensional medical image;
set apexes of a second ROI based on some fixed points included in the fixed points;
receive an instruction from an input device used by a user; and
change, in accordance with the received instruction, at least one of the apexes based on at least one of the fixed points other than the some fixed points while maintaining positions of the fixed points.

2. The apparatus according to claim 1, wherein
the processing circuitry is configured to:
cause a display unit to display, before the position of the boundary of the second ROI is changed, a first rendering image obtained by applying rendering processing to three-dimensional image data representing a part of the three-dimensional shape of the target region and the second ROI before the position of the boundary is changed; and cause the display unit to display, after the position of the boundary of the second ROI is changed, a second rendering image obtained by applying the rendering processing to the three-dimensional image data representing the part of the three-dimensional shape of the target region and the second ROI after the position of the boundary is changed.

3. The apparatus according to claim 2, wherein the processing circuitry is configured to receive the instruction with respect to the first rendering image displayed on the display unit.

4. The apparatus according to claim 3, wherein
the processing circuitry is configured to:
perform tracking processing between the first medical image and a second medical image collected in a time phase different from that of the first medical image based on the positions of the fixed points;
calculate motion information for the second ROI based on a result of the tracking processing; and
cause the display unit to display the motion information for the second ROI in a predetermined display form.

5. The apparatus according to claim 4, wherein the target region is a heart chamber.

6. The apparatus according to claim 3, wherein line segments connecting adjacent fixed points are depicted in the first rendering image and the second rendering image.

7. The apparatus according to claim 3, wherein the fixed points are depicted in the first rendering image and the second rendering image.

8. The apparatus according to claim 1, wherein the boundary on the three-dimensional shape of the target region is set so as to pass through at least one of the fixed points.

9. The apparatus according to claim 1, wherein the boundary is changed so that the changed boundary passes through at least one of the fixed points that the previous boundary does not pass through.

10. The apparatus according to claim 1, wherein
the processing circuitry is configured to:
receive, as the instruction, an instruction to adjust a position or positions of at least either of a side of the boundary of the second ROI and an apex corresponding to the end of the side; and
adjust the position or positions so that the side, or the apex corresponding to the end of the side, to be adjusted in position by the instruction coincides with any of the fixed points.

11. The medical diagnosis apparatus according to claim 10, wherein
the processing circuitry is configured to:
further set identification information identifying each of the apex and the boundary:
receive, as the instruction, an instruction to specify the identification information.

12. The apparatus according to claim 1, wherein the processing circuitry is configured to set, as the second ROI, a region group including regions adjacent to one another.

13. The apparatus according to claim 1, wherein the processing circuitry is configured to set the second ROI according to a photographed region of a heart in the first medical image.

14. The apparatus according to claim 1, wherein
the processing circuitry is configured to:
cause a display unit to display a polar map of a heart associated with the second ROI; and
receive, according to control applied to an apex or a boundary on the polar map displayed on the display unit, adjustment of position information of an apex or a boundary corresponding to the apex or the boundary on the polar map.

15. The apparatus according to claim 1, wherein the processing circuitry is configured to further calculate, each time the boundary of the second ROI is adjusted, a value indicating motion information of the positions included in the second ROI after being adjusted.

16. The apparatus according to claim 15, wherein the processing circuitry is configured to cause a display unit to display the value, each time the value is calculated.

17. The apparatus according to claim 1, wherein the apparatus is an ultrasound diagnostic imaging apparatus.

18. An image processing apparatus comprising:
processing circuitry configured to:
discretely arrange fixed points framing a first region of interest (ROI) corresponding to a target region in a first three-dimensional medical image based on data of a three-dimensional region;
set apexes of a second ROI based on some fixed points included in the fixed points;
receive an instruction from an input device used by a user; and
change, in accordance with the received instruction, at least one of the apexes based on at least one of the fixed points other than the some fixed points while maintaining positions of the fixed points.

19. A method for image processing executed by an image processing apparatus, the method comprising:
discretely arranging fixed points framing a first region of interest (ROI) corresponding to a target region in a first three-dimensional medical image based on data of a three-dimensional region;
setting apexes of a second ROI based on some fixed points included in the fixed points;
receiving an instruction from an input device used by a user; and
changing, in accordance with the received instruction, at least one of the apexes based on at least one of the fixed points other than the some fixed points while maintaining positions of the fixed points.

20. The apparatus according to claim 1, wherein
the second ROI corresponds to at least one of a plurality of regions formed by dividing the first ROI.

* * * * *